United States Patent
Birnboim et al.

(10) Patent No.: US 12,214,299 B2
(45) Date of Patent: Feb. 4, 2025

(54) COMPOSITION, SYSTEM AND METHOD FOR REMOVAL OF DETERGENTS FROM AQUEOUS SOLUTIONS

(71) Applicant: DNA GENOTEK INC., Kanata (CA)

(72) Inventors: Hyman Chaim Birnboim, Ottawa (CA); Rajeev Mani Nepal, Burnaby (CA); Bitapi Ray, Stittsville (CA); Jessica Lynne Gage, Kanata (CA); Christopher Gordon Askew, Ottawa (CA)

(73) Assignee: DNA GENOTEK INC., Kanata (CA)

( * ) Notice: Subject to any disclaimer, the term of this patent is extended or adjusted under 35 U.S.C. 154(b) by 1274 days.

(21) Appl. No.: 16/305,191

(22) PCT Filed: May 30, 2017

(86) PCT No.: PCT/CA2017/050655
§ 371 (c)(1),
(2) Date: Nov. 28, 2018

(87) PCT Pub. No.: WO2017/205971
PCT Pub. Date: Dec. 7, 2017

(65) Prior Publication Data
US 2020/0316493 A1    Oct. 8, 2020

Related U.S. Application Data

(60) Provisional application No. 62/343,293, filed on May 31, 2016.

(51) Int. Cl.
*B01D 17/04* (2006.01)
*B01D 17/02* (2006.01)
(Continued)

(52) U.S. Cl.
CPC ....... *B01D 17/047* (2013.01); *B01D 17/0217* (2013.01); *C02F 1/385* (2013.01);
(Continued)

(58) Field of Classification Search
None
See application file for complete search history.

(56) References Cited

U.S. PATENT DOCUMENTS 6,815,541 B1 * 11/2004 Usui .................. C07H 1/08
                                                  536/25.4
6,858,224 B2    2/2005 Wheeler et al.
(Continued)

FOREIGN PATENT DOCUMENTS

CN    1503910 A    6/2004
CN    102939381 A   2/2013
(Continued)

OTHER PUBLICATIONS

International Search Report and Written Opinion dated Aug. 24, 2017 of corresponding International application No. PCT/CA2017/050655; 13 pgs.
(Continued)

*Primary Examiner* — Peter Keyworth
(74) *Attorney, Agent, or Firm* — Maier & Maier, PLLC

(57) ABSTRACT

A system, composition, method and kit for removing a detergent, such as an anionic detergent, from an aqueous solution, comprising a salt, a water immiscible alcohol of Formula I:

$$R^1\text{—OH} \quad \text{(Formula I)}$$

where R1 is an optionally substituted, linear, branched or cyclic C4-C12 alkyl; and a water immiscible halocarbon, wherein said halocarbon is miscible with said alcohol of Formula I. The system can be used on aqueous solutions that contain detergents (such as Sodium Dodecyl Sulphate
(Continued)

(SDS), for example), and any detergent-associated or detergent-bound molecules that may be present in the aqueous solution, to form an aqueous phase and a non-aqueous phase, for effectively removing the detergent and any detergent-associated or detergent-bound molecules, and sequestering them into the non-aqueous phase.

14 Claims, 21 Drawing Sheets

(51) Int. Cl.
  *C02F 1/38* (2023.01)
  *C02F 1/40* (2023.01)
  *C07C 303/44* (2006.01)
  *C12Q 1/6806* (2018.01)
  *C02F 101/30* (2006.01)

(52) U.S. Cl.
  CPC .............. *C02F 1/40* (2013.01); *C07C 303/44* (2013.01); *C12Q 1/6806* (2013.01); *C02F 2101/301* (2013.01)

(56) References Cited

U.S. PATENT DOCUMENTS

| | | | |
|---|---|---|---|
| 7,482,116 B2 | 1/2009 | Birnboim | |
| 2002/0119483 A1* | 8/2002 | Wheeler | G01R 33/46 |
| | | | 435/6.12 |
| 2002/0192651 A1 | 12/2002 | Wheeler et al. | |
| 2009/0123976 A1 | 5/2009 | Birnboim et al. | |
| 2010/0099149 A1 | 4/2010 | Birnboim et al. | |

FOREIGN PATENT DOCUMENTS

| | | | | |
|---|---|---|---|---|
| DE | 19720153 | A1 | 12/1997 | |
| EP | 0338591 | A1 | 10/1989 | |
| RU | 2101354 | C1 | 1/1998 | |
| WO | WO-9412657 | A1 * | 6/1994 | ......... C12N 15/1003 |
| WO | 9600228 | A1 | 1/1996 | |
| WO | 2007/051303 | A1 | 5/2007 | |
| WO | 2015179976 | A1 | 12/2015 | |

OTHER PUBLICATIONS

International Preliminary Report on Patentability dated Sep. 20, 2018 of corresponding International application No. PCT/CA2017/050655; 49 pgs.
Office Action issued on Aug. 14, 2024, in corresponding Canadian Application No. 3,026,134, 5 pages.
Birnboim, "A Rapid Alkaline Extraction Method for the Isolation of Plasmid DNA", Isolation of Plasmid DNA, Methods in Enzymology, Academic Press, Inc., 1983, vol. 100, pp. 243-255.
Weyant et al., "Effect of Ionic and Nonionic Detergents on the Taq Polymerase", BioFeedback, BioTechniques, Sep. 1990, vol. 9, No. 3, pp. 308-309.
Rossen et al., "Inhibition of PCR by Components of Food Samples, Microbial Diagnostic Assays and DNA-Extraction Solutions", International Journal of Food Microbiology, Elsevier Science Publishers B.V., 1992, vol. 17, pp. 37-45.
Bickley et al., "Inhibitors and Enhancers of PCR", Analytical Molecular Biology: Quality and Validation. Royal Society of Chemistry, 1999, pp. 81-102.
Rusconi et al., "Quantification of Sodium Dodecyl Sulfate in Microliter-vol. Biochemical Samples by Visible Light Spectroscopy", Analytical Biochemistry, Academic Press, Jul. 2, 2001, vol. 295, pp. 31-37.
Office Action issued on Oct. 3, 2022, in corresponding Australian Application No. 2017274602, 5 pages.
Office Action issued on Mar. 17, 2023, in corresponding Canadian Application No. 3,026, 134, 4 pages.
Office Action issued on Dec. 22, 2021, in corresponding Chinese Application No. 201780033489.4, 8 pages.
Office Action issued on Sep. 14, 2022, in corresponding Chinese Application No. 201780033489.4, 23 pages.
Office Action issued on Mar. 1, 2023, in corresponding Chinese Application No. 201780033489.4, 23 pages.
Extended Search Report issued on Jan. 23, 2020, in corresponding European Application No. 17805442.5, 16 pages.
Office Action issued on Mar. 29, 2023, in corresponding European Application No. 17805442.5, 6 pages.
Office Action issued on Mar. 13, 2024, in corresponding European Application No. 17805442.5, 5 pages.
Office Action issued on Jun. 8, 2021, in corresponding Japanese Application No. 2018-562570, 7 pages.
Office Action issued on Apr. 5, 2022, in corresponding Japanese Application No. 2018-562570, 6 pages.
Office Action issued on Nov. 14, 2023, in corresponding Japanese Application No. 2018-562570, 4 pages.
Office Action issued on Aug. 8, 2023, in corresponding Japanese Application No. 2022-125531, 6 pages.
Office Action issued on Nov. 11, 2024, in corresponding Australian Application No. 2023237224, 5 pages.
Office Action issued on Nov. 19, 2024, in corresponding European Application No. 17 805 442.5, 6 pages.

\* cited by examiner

COMPOSITION, SYSTEM AND METHOD FOR REMOVAL OF DETERGENTS FROM AQUEOUS SOLUTIONS

CROSS-REFERENCE TO RELATED APPLICATION

This application is the national phase application of International Application No. PCT/CA2017/050655, filed on May 30, 2017, which claims priority to U.S. Provisional Application No. 62/343,293, filed on May 31, 2016. The entire contents of International Application No. PCT/CA2017/050655 are herein incorporated by reference.

FIELD OF THE INVENTION

The present application pertains to a composition, system, method and kit for removing a detergent from an aqueous solution. The composition, system, method and kit of the present application may also be used for removing detergent-associated and/or detergent-bound molecules from aqueous solutions.

BACKGROUND

Sodium Dodecyl Sulphate (SDS) is an anionic detergent used in many cleaning and personal hygiene products. It is also commonly used in molecular biology applications such as SDS-PAGE (SDS-polyacrylamide gel electrophoresis) for studying proteins, in nucleic acid purification procedures, as well as in nucleic acid stabilization compositions.

When working with biological samples from which the release of nucleic acids is sought, the ability to dissolve cellular and particle membranes due to its amphipathic property is exploited in lysis buffers. Additionally, SDS binds tightly to proteins and is used to disrupt protein-nucleic acid interactions during extraction procedures. For example, SDS disrupts ionic interactions between positively-charged histones and the negatively-charged phosphates in the backbone of nucleic acids, thus helping to separate nucleic acids from proteins. Many common laboratory protocols for purifying deoxyribonucleic acid (DNA) make use of SDS, for example, conventional ethanol precipitation of DNA (Sambrook, Molecular Cloning: A Laboratory Manual (Third Edition)), lithium chloride precipitation (Sambrook, Molecular Cloning: A Laboratory Manual (Third Edition)) or the SDS-alkaline denaturation method for obtaining plasmid DNA (Birnboim, H. C. (1983) *A Rapid Alkaline Extraction Method for the Isolation of Plasmid DNA.*, Methods Enzymol. 100, 243-55).

The ability of SDS to denature proteins by binding tightly to them and disrupting their structure results in the inactivation of most enzymes, including nucleases. This property is exploited for purposes of stabilizing and preserving nucleic acids in biological samples, as taught by Birnboim et al. in U.S. Pat. No. 7,482,116, US2010099149 and US2009123976. However, this property has the undesired effect of inhibiting enzyme-dependent reactions in subsequent applications using the nucleic acids if SDS is not thoroughly removed.

The abilities and characteristics of SDS are well known to those who practice the art of biochemistry and molecular biology. Most procedures to extract and purify nucleic acids do so by removing the nucleic acids from solution, leaving behind inhibitors and impurities. For example, addition of 1 to 2 volumes of ethanol to an aqueous solution causes the nucleic acids to precipitate, where they can be recovered from the pellet after a centrifugation step. Alternatively, nucleic acids can be bound to solid matrices, e.g., silica particles, from which they can be subsequently eluted. The resultant purified nucleic acid can be used in downstream applications such as the polymerase chain reaction (PCR), reverse transcriptase-PCR (RT-PCR), sequencing library preparation or sequencing.

There have been numerous attempts over the past 5 or 6 decades to simplify and improve procedures for the extraction and purification of nucleic acids. Typically, the reagents used in these procedures are inhibitory to downstream applications that utilize the purified nucleic acids. Therefore, reagents added to the initial sample during processing must be completely removed. For example, low concentrations of SDS are inhibitory to the Taq DNA polymerase used in PCR reactions. As little as 0.01% weight per volume of SDS in the final PCR is inhibitory, as reported by Weyant et al. 1990; Rossen et al. 1992; Saunders et al. 1999. This has been confirmed below. Several products exist in the market to remove SDS from samples (e.g., SDS Away™ [ProteaBiosciences]; Detergent-Out™ [Millipore]; SDS-Out™ [Pierce Biotechnology Inc.] are three examples), but these are optimized and formulated to remove SDS that is tightly bound to proteins rather than SDS present in solutions of nucleic acids.

At present there are 3 main classes of commercially available nucleic acid purification kits: (i) phenol-based extraction methods (e.g., Trizol™ [Invitrogen] and TriReagent™ [Molecular Research Centre, Inc.]), (ii) guanidinium-based binding of nucleic acids to solid matrices (e.g., silica surfaces on magnetic beads and columns) and (iii) SDS-based methods. Some SDS-based chemistries are incompatible with guanidinium-based chemistries because mixing the two reagents results in the precipitation of SDS as the insoluble guanidinium salt. The presence of SDS during a phenol/chloroform extraction has been observed to cause a milky precipitate to form. However, it has been observed that an SDS-containing sample could be processed in phenol/chloroform-based or guanidinium-based chemistries, provided the SDS was substantially removed beforehand. A simple way to lower the SDS concentration would be to dilute the sample to a level where SDS no longer precipitates, but that would introduce a need to concentrate the sample at a later step. Simple and rapid removal of SDS from an aqueous sample is an unmet need in the biochemistry and molecular biology arts.

Therefore, there remains a need for a composition and method that, when used on any aqueous solution that contains an anionic detergent, can effectively remove the detergent to barely detectable levels (less than 0.01% wt/vol) in an easy, rapid and efficient manner.

This background information is provided for the purpose of making known information believed by the applicant to be of possible relevance to the present invention. No admission is necessarily intended, nor should be construed, that any of the preceding information constitutes prior art against the present invention.

SUMMARY

An object of the present application is to provide a composition, system, method and kit for removal of a detergent from an aqueous solution. The composition, system, method and kit may also be used for removal of detergent-associated or detergent-bound molecules, including proteins, from an aqueous solution.

In accordance with one aspect, there is provided a detergent removal system comprising: (a) a salt; (b) a water immiscible alcohol of Formula I

   I where $R^1$ is an optionally substituted, linear, branched or cyclic $C_4$-$C_{12}$ alkyl; and (c) a water immiscible halocarbon, wherein the halocarbon is miscible with the alcohol. Optionally, the salt is a quaternary ammonium salt or an alkali metal salt. In certain embodiments, the detergent is an anionic detergent. In certain embodiments, the system may also be used to remove detergent-associated and/or detergent-bound molecules that may be present in the aqueous solution.

In accordance with another aspect, there is provided a method of removing a detergent from an aqueous solution comprising said detergent, said method comprising the step of mixing the aqueous solution with: a salt; a water immiscible alcohol of Formula I

   I where $R^1$ is an optionally substituted, linear, branched or cyclic $C_4$-$C_{12}$ alkyl; and a water immiscible halocarbon, wherein the halocarbon is miscible with the alcohol, to form a two-phase mixture, wherein substantially all of the detergent is in the non-aqueous phase. In certain embodiments, the detergent is an anionic detergent. In certain embodiments, the method may also be used to remove detergent-associated and/or detergent-bound molecules that may be present in the aqueous solution.

In accordance with another aspect, there is provided a biphasic composition formed from mixing: a salt; a water immiscible alcohol of Formula I

   I where $R^1$ is an optionally substituted, linear, branched or cyclic $C_4$-$C_{12}$ alkyl; and a water immiscible halocarbon; with an aqueous solution comprising a detergent, wherein substantially all of the detergent is in the non-aqueous phase. In certain embodiments, the detergent is an anionic detergent. In certain embodiments, the non-aqueous phase of the biphasic composition may also comprise detergent-associated and/or detergent-bound molecules.

In accordance with another aspect, there is provided a kit for removal of a detergent from an aqueous solution comprising said detergent, said kit comprising: a salt; a water immiscible alcohol of Formula I

   I where $R^1$ is an optionally substituted, linear, branched or cyclic $C_4$-$C_{12}$ alkyl; a water immiscible halocarbon, wherein said halocarbon is miscible with said alcohol of Formula I; at least one reagent container; and, optionally, instruction(s) for use. In certain embodiments, the detergent is an anionic detergent. In certain embodiments, the kit may also be used to remove detergent-associated and/or detergent-bound molecules from the aqueous solution that may be present.

The present composition, system, method and kit may, thus, ideally be used to remove inhibitors from aqueous solutions, i.e. inhibitors that inhibit reactions such as downstream applications, including, but not limited to, PCR (including RT-PCR), library preparation, and nucleotide sequencing. Inhibitors may include, for example, enzymatic inhibitors, e.g., inhibitors of enzyme-dependent reactions in subsequent applications, for example.

In certain embodiments, at least a portion of the aqueous phase (i.e., the phase that does not substantially contain the detergent, and detergent-associated or detergent-bound molecules, if present) may be used directly for downstream applications including, but not limited to, PCR (including RT-PCR), library preparation, and nucleotide sequencing.

BRIEF DESCRIPTION OF THE FIGURES

For a better understanding of the present invention, as well as other aspects and further features thereof, reference is made to the following description which is to be used in conjunction with the accompanying drawings, where.

Figure 8:
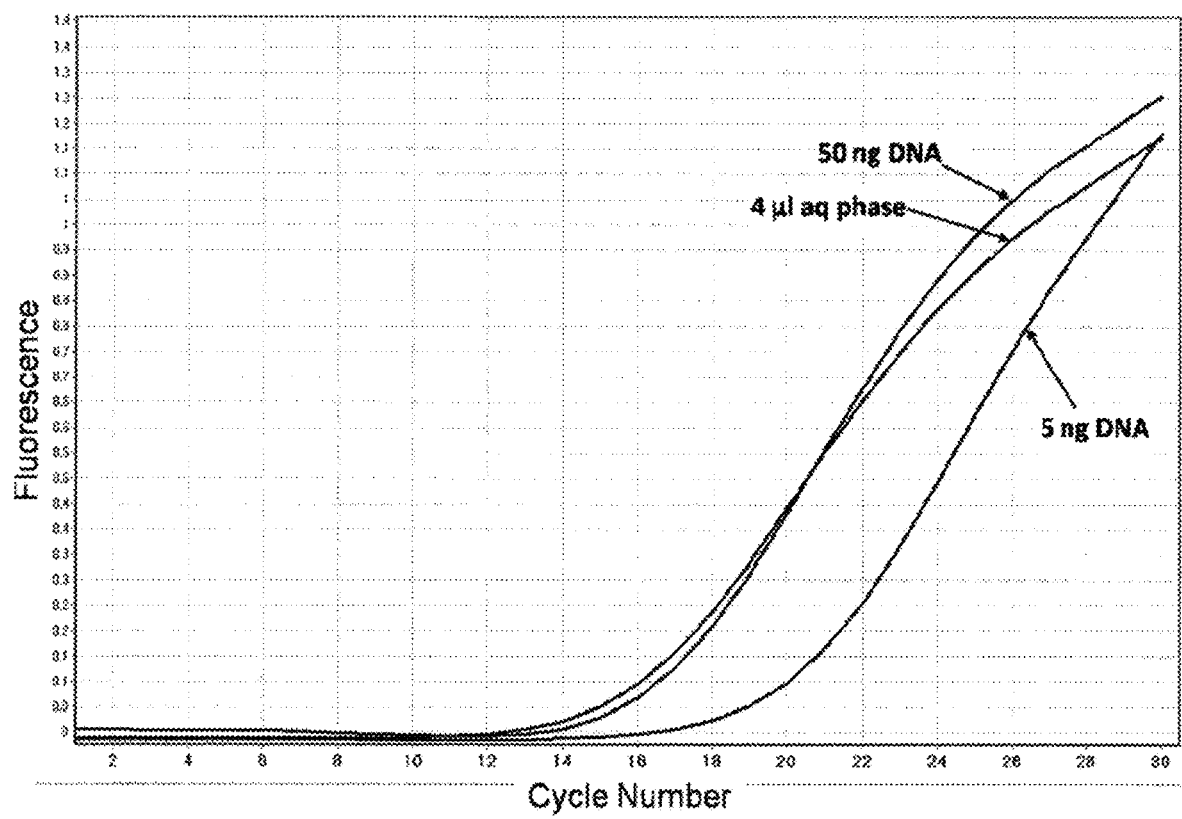
Figure 9:
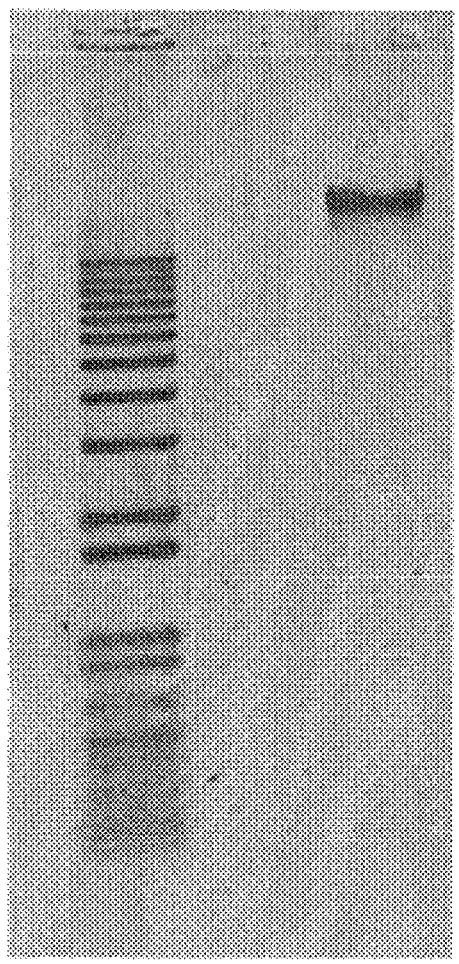
Figure 10:
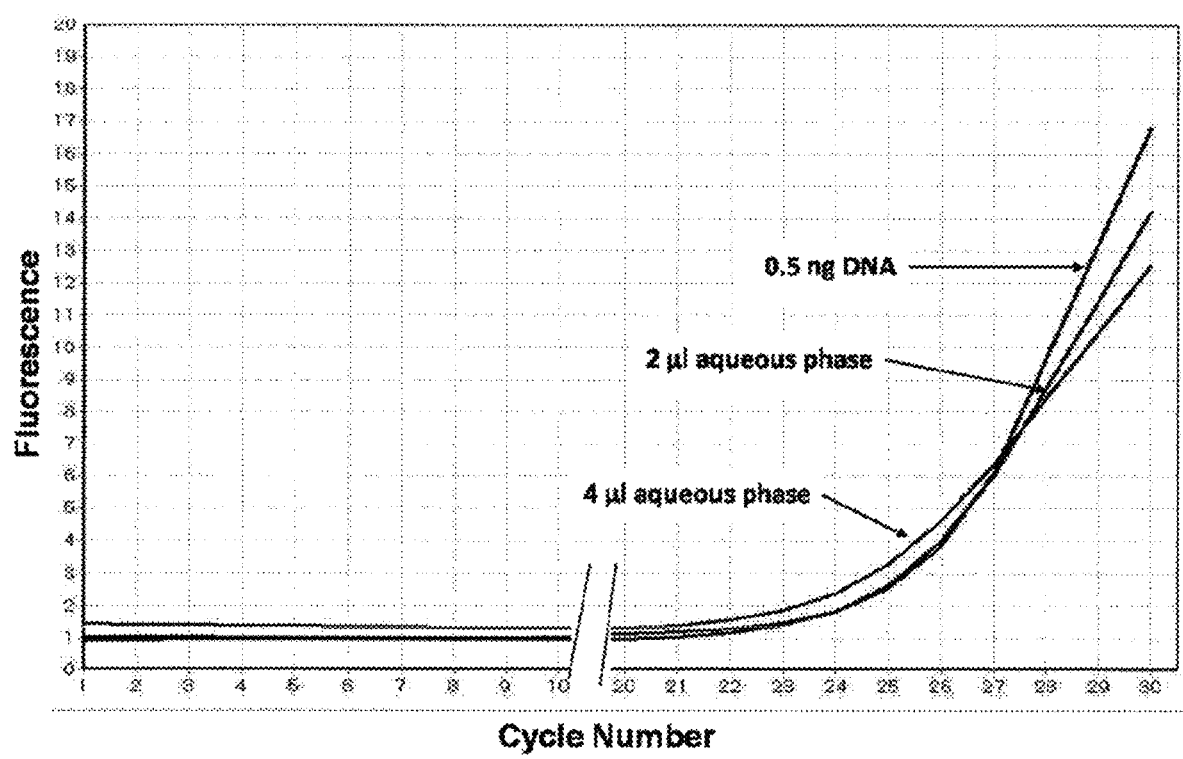
Figure 11:
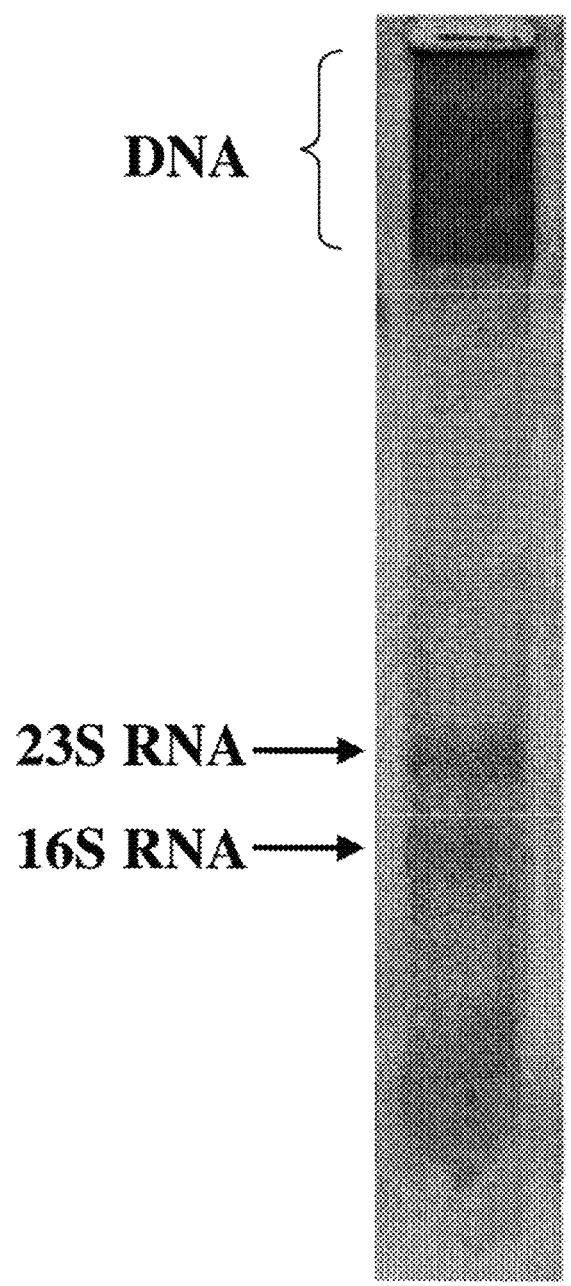
Figure 12:
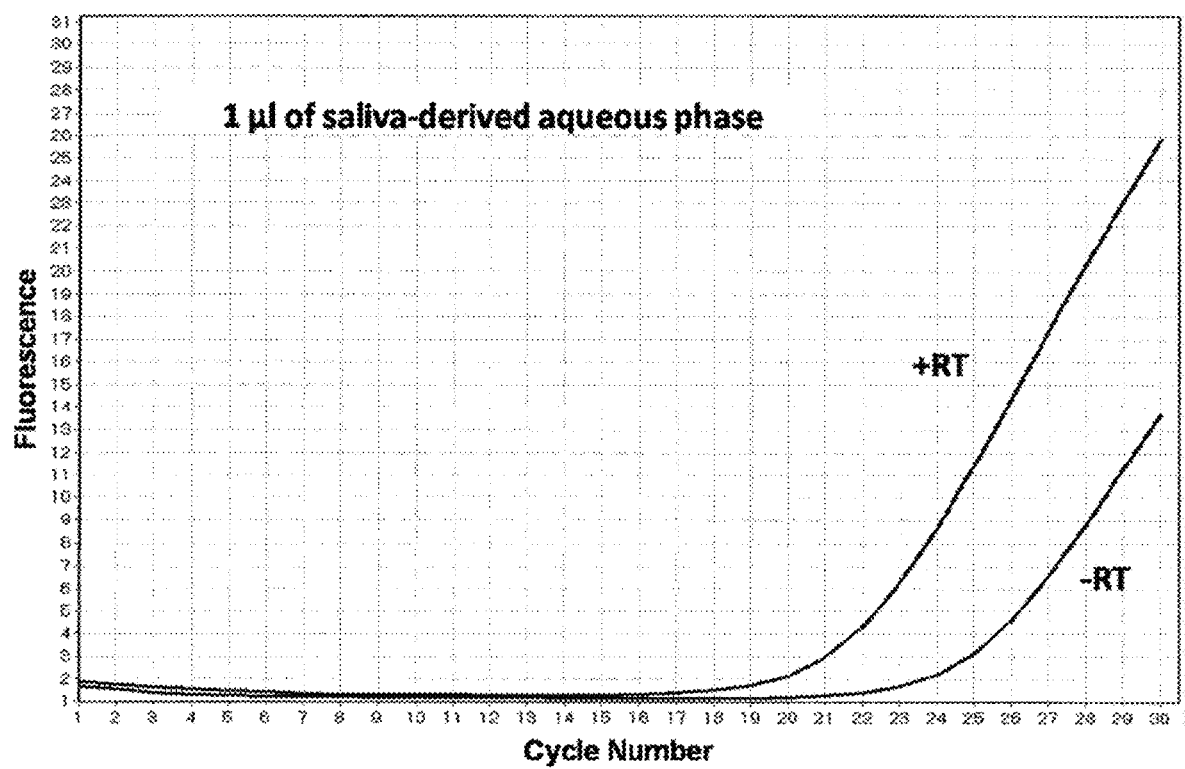
Figure 13:
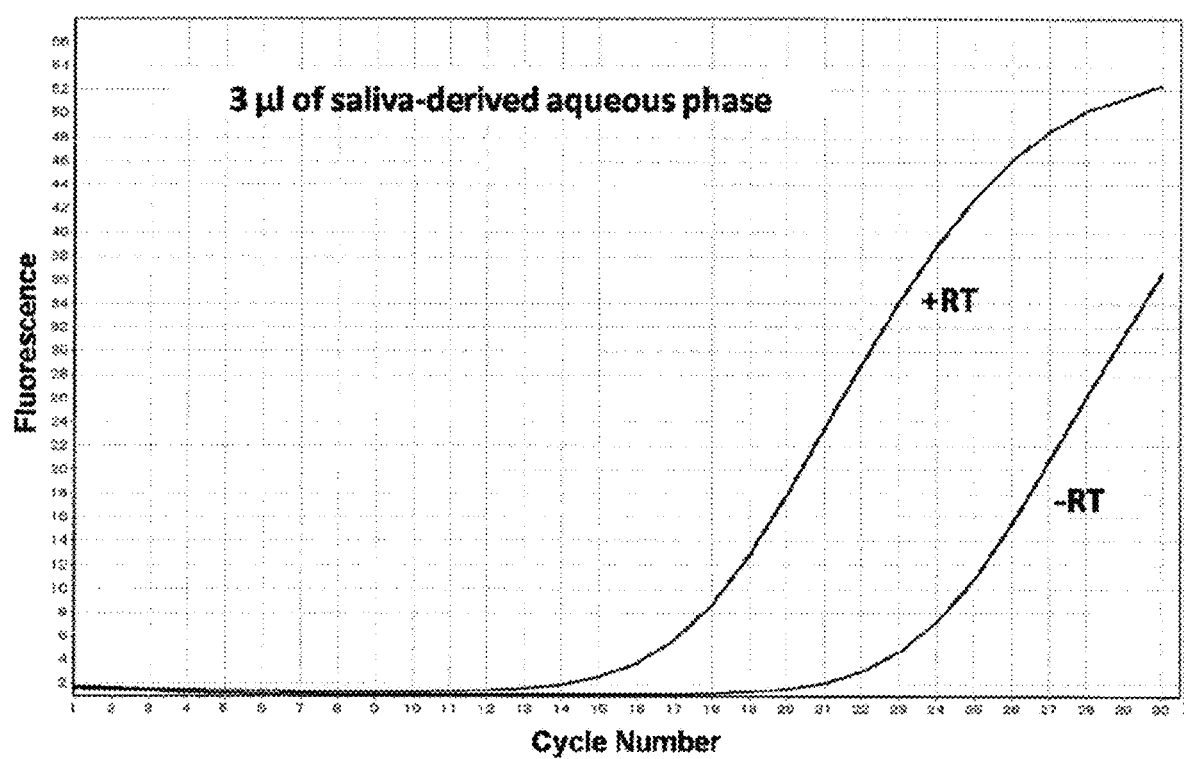
Figure 14:
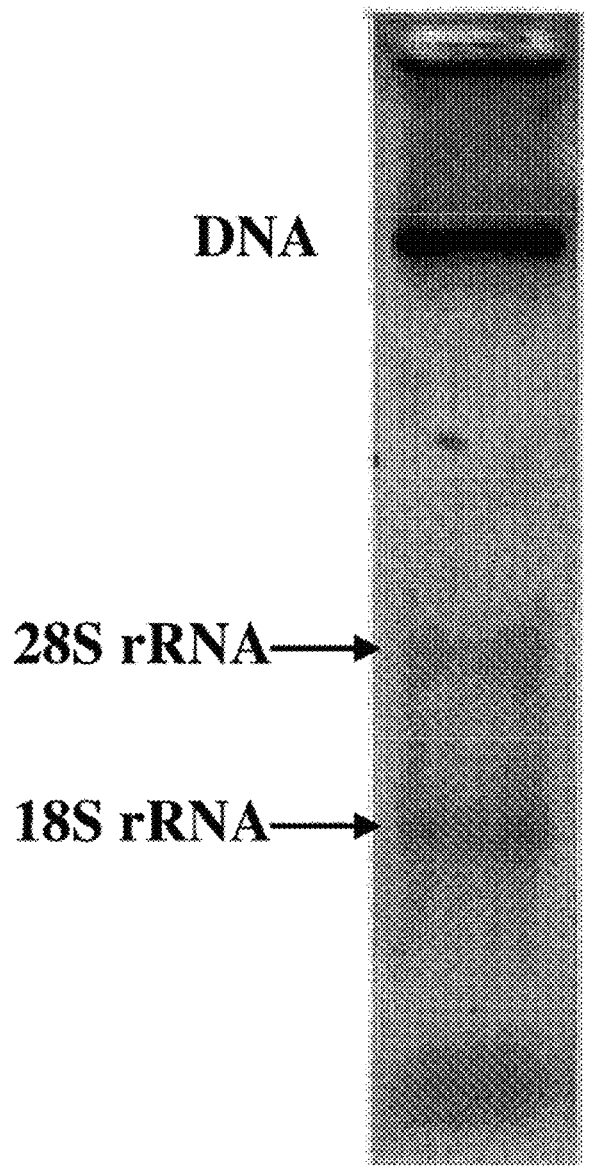
Figure 15:
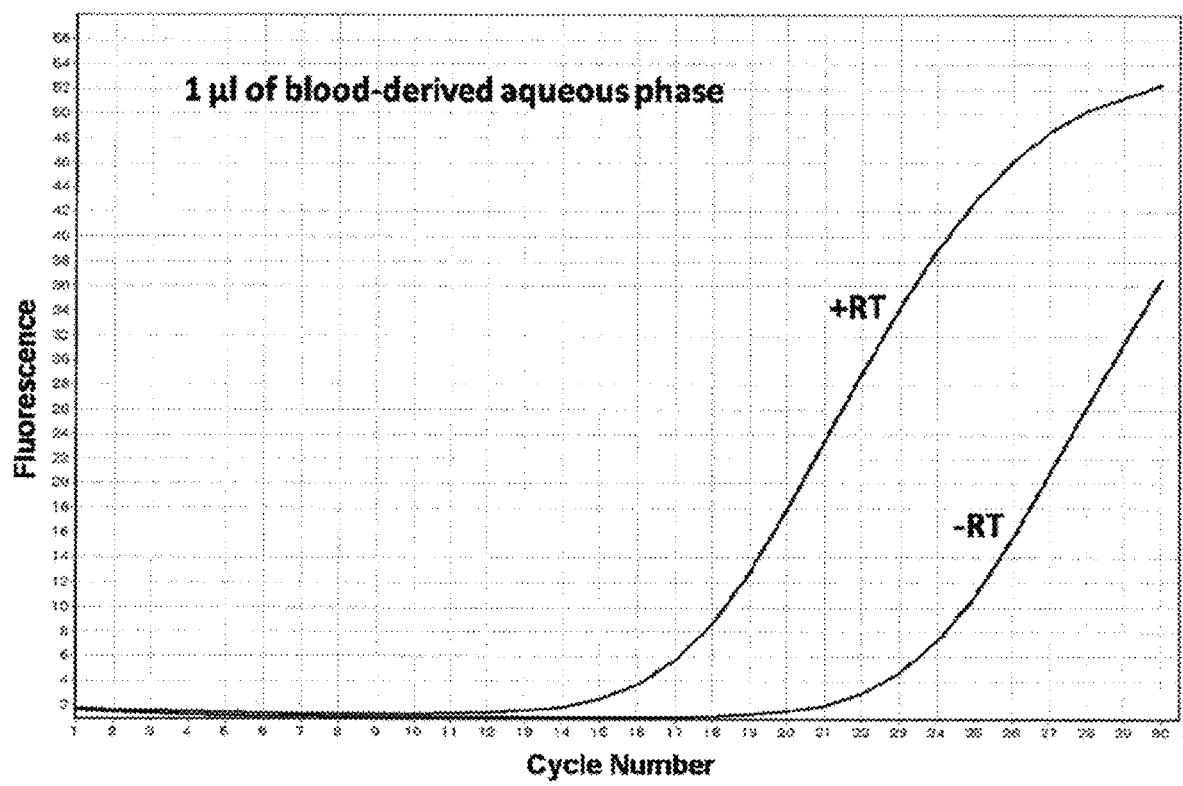
Figure 16:
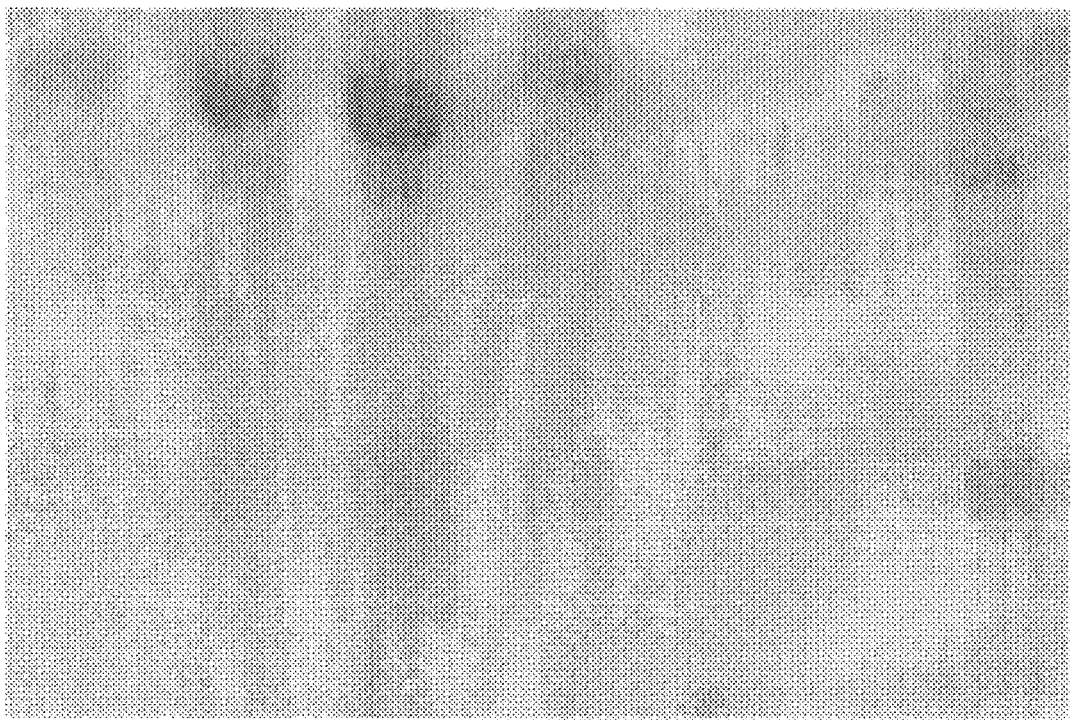

Kb+ DNA ladder, indicating that the detergent removal composition did not cause degradation of DNA;

FIG. 8 shows the results of qPCR performed on an aliquot of the aqueous phase from a saliva sample collected into a detergent solution and treated with a detergent removal composition, alongside two standard controls of known amounts of DNA; the results demonstrate that DNA remaining in the aqueous phase after detergent removal treatment was suitable for use in qPCR;

FIG. 9 is a photograph of an agarose gel stained with SybrGold™ (Invitrogen) following electrophoresis of an aliquot of the aqueous phase from a blood sample collected into a detergent solution and treated with a detergent removal composition; high molecular weight DNA can be seen in the sample lane alongside a 1 Kb+ DNA ladder, indicating that the detergent removal composition did not cause degradation of DNA;

FIG. 10 shows the results of qPCR performed on two different sized aliquots of the aqueous phase from a blood sample collected into a detergent solution and treated with a detergent removal composition, alongside an aliquot from a control containing a known amount of DNA; the results show that DNA remaining in the aqueous phase after detergent removal treatment was suitable for use in qPCR;

FIG. 11 is a photograph of an agarose gel stained with SybrGold™ (Invitrogen) following electrophoresis of an aliquot of the aqueous phase from a saliva sample collected into a detergent solution and treated with a detergent removal composition; bacterial 16S and 23S ribosomal RNA bands, originating from bacterial cells in saliva, can be seen on the gel, which indicates that bacterial RNA was not degraded by the detergent removal treatment;

FIG. 12 shows the results of qPCR of the Reverse Transcriptase products prepared from a 1 µl aliquot of the aqueous phase taken from a saliva sample collected into a detergent solution and treated with a detergent removal composition;

FIG. 13 shows the results of qPCR of the Reverse Transcriptase products prepared from a 3 µl aliquot of the aqueous phase taken from a saliva sample collected into a detergent solution and treated with a detergent removal composition;

FIG. 14 is a photograph of an agarose gel stained with SybrGold™ (Invitrogen) following electrophoresis of an aliquot of the aqueous phase from a blood sample collected into a detergent solution and treated with a detergent removal composition; human 18S and 28S ribosomal RNA bands can be seen, indicating that human RNA was not degraded;

FIG. 15 shows the results of qPCR of the Reverse Transcriptase products prepared from a 1 µl aliquot of the aqueous phase of a blood sample collected into a detergent solution and treated with a detergent removal composition;

FIG. 16 is a photograph of a polyacrylamide gel stained with Coomassie blue to reveal protein bands following SDS-PAGE; aliquots of the same blood sample collected into a standard EDTA tube were removed and treated with various components of the detergent removal composition described herein: Lane 1 contains the protein molecular weight marker, Lane 2 is empty, Lane 3 contains 0.5 µl of lysed blood sample prior to detergent removal, Lane 4 is empty. Lane 5 contains 1 µl of lysed blood sample prior to detergent removal, Lane 6 is empty, Lane 7 contains 7.5 µl of aqueous phase after treatment of a lysed blood sample with BDCM only, Lane 8 is empty, Lane 9 contains 7.5 µl of aqueous phase after treatment of a lysed blood sample with a 3:7 (vol/vol) mix of 1-pentanol: BDCM, Lane 10 contains 7.5 µl of aqueous phase after treatment of a lysed blood sample with a 1:1 (vol/vol) mix of 1-pentanol: BDCM, Lane 11 contains 7.5 µl of aqueous phase after treatment of a lysed blood sample with a 7:3 (vol/vol) mix of 1-pentanol: BDCM, and Lane 12 contains 7.5 µl of aqueous phase after treatment of a lysed blood sample with 1-pentanol only.

Figure 17:
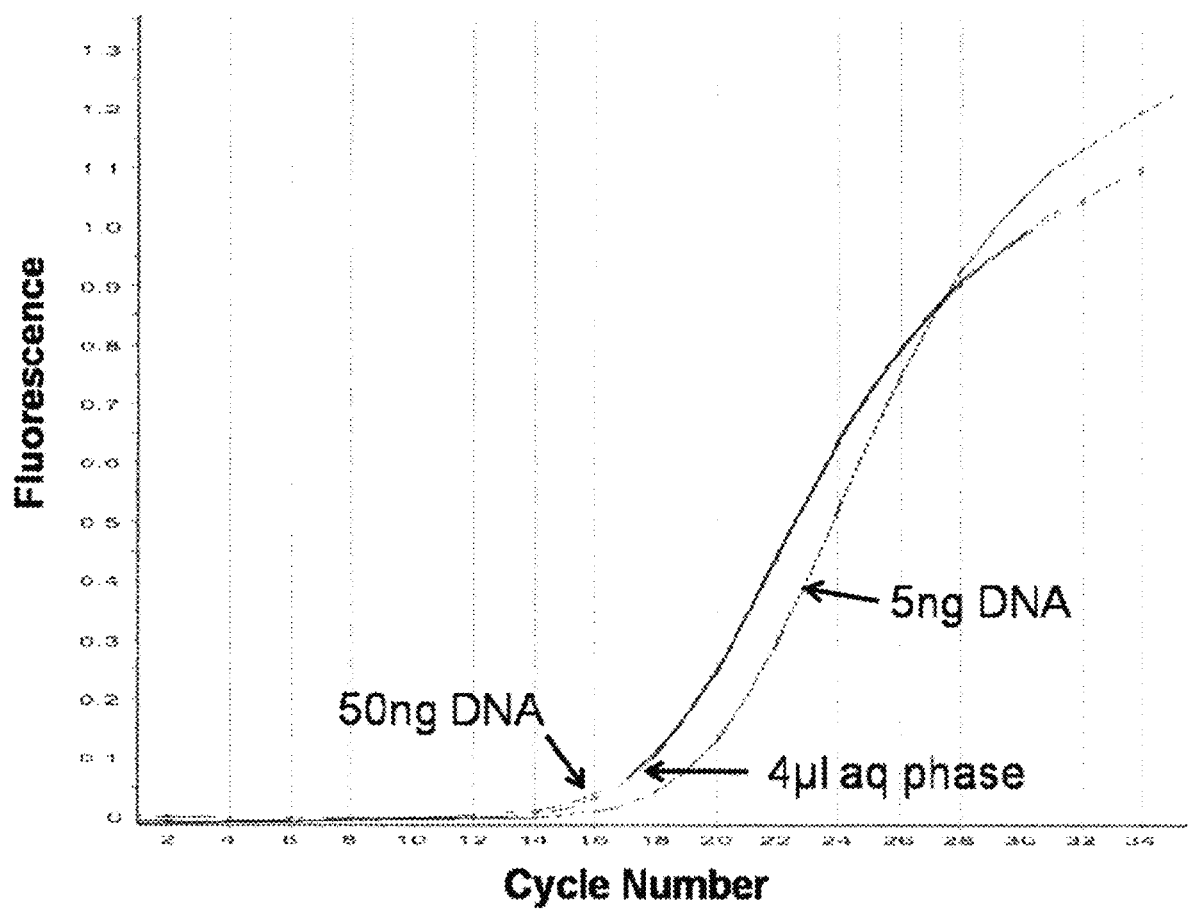

FIG. 17 depicts the treatment of a saliva sample collected into an aqueous solution comprising 2% Sarkosyl with a detergent removal composition; the detergent removal composition used comprised a 1:0.8 mix of 1-pentanol and (poly)chlorotrifluoroethylene with 200 mM ammonium chloride and the results show that Sarkosyl was efficiently removed even in the presence of this biological sample.

Figure 18A:
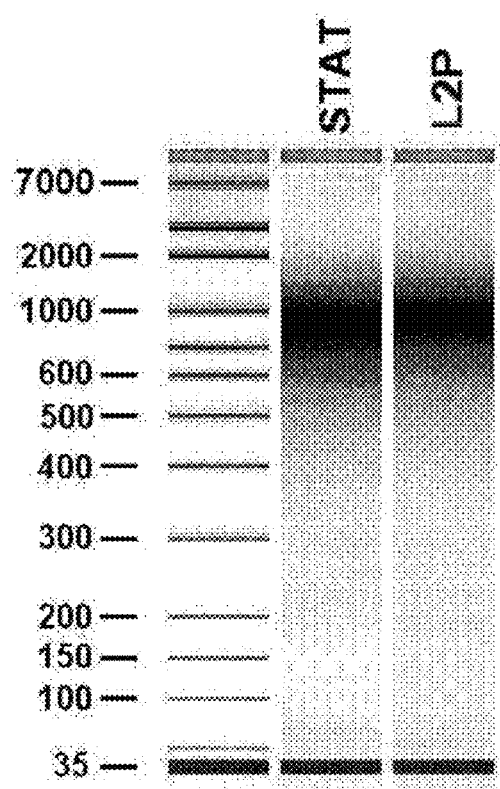
Figure 18B:
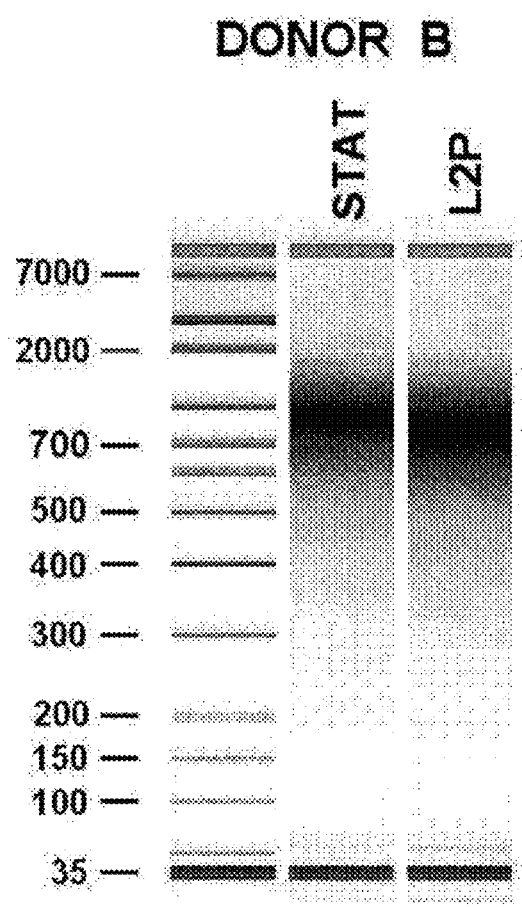
Figure 19A:
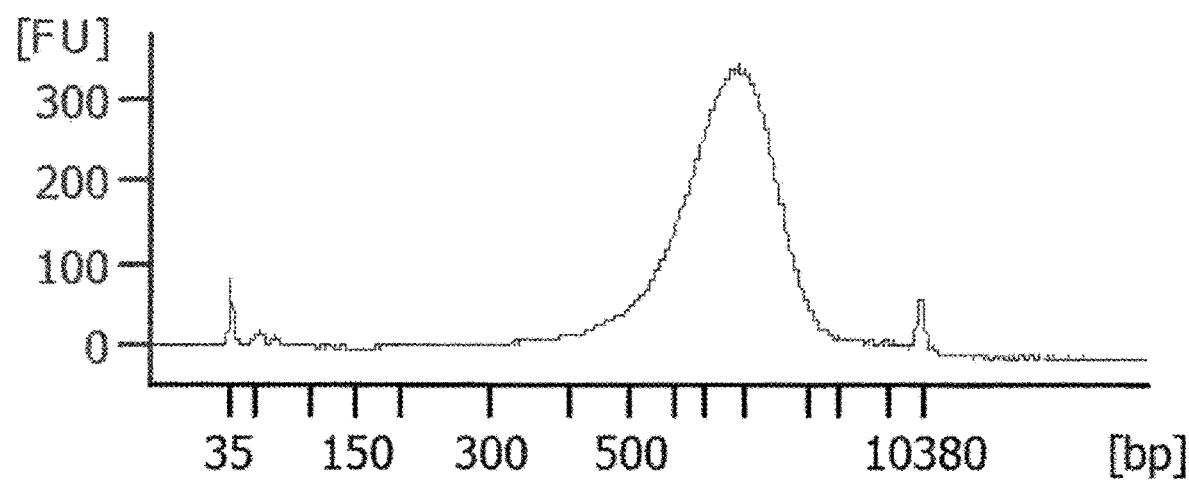
Figure 19B:
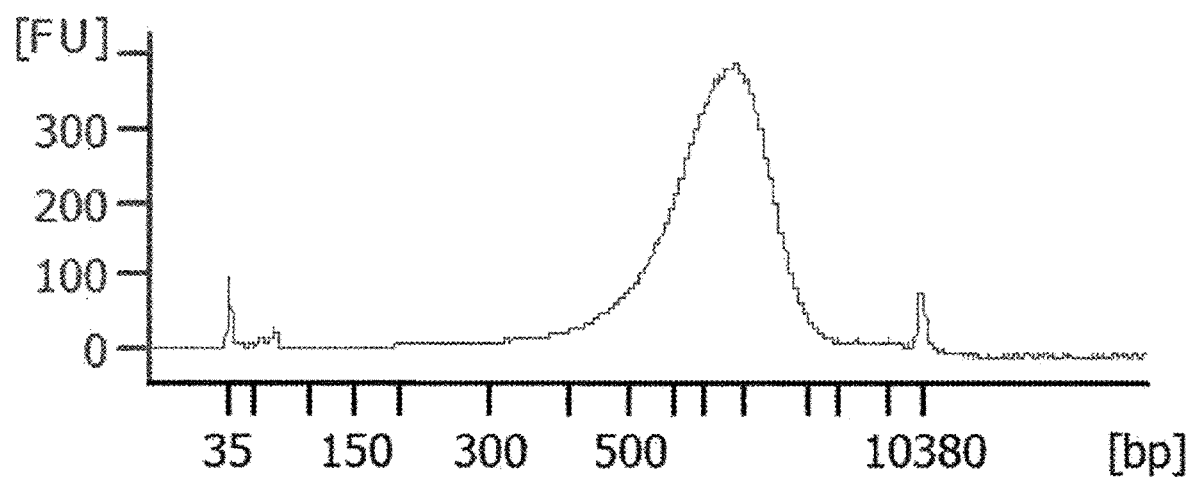
Figure 19C:
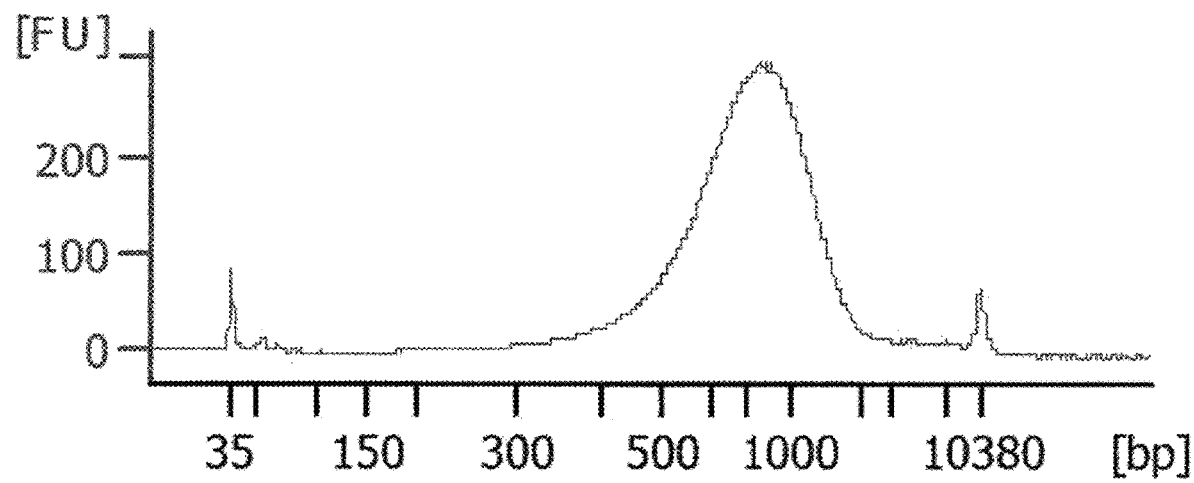
Figure 19D:
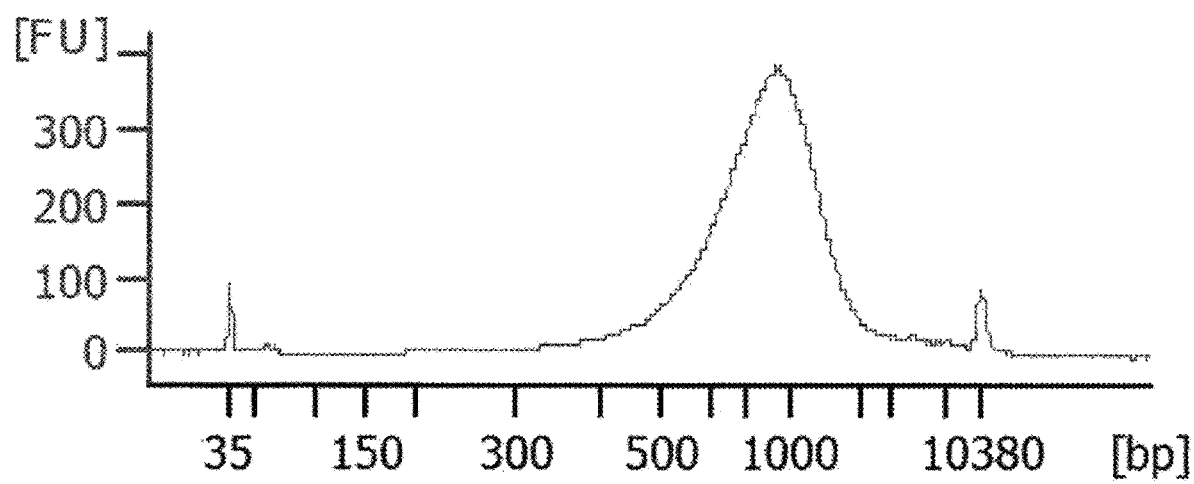

FIG. 18 depicts the Bioanalyzer gel images of STAT- and prepIT·L2P-treated saliva samples from donor A (FIG. 18A) and donor B (FIG. 18B).

FIG. 19 depicts the Bioanalyzer gel traces of the library preps constructed from saliva samples of 2 donors. FIG. 19A depicts the trace of the library prep constructed from the saliva sample of donor A purified with Oragene/prepIT·L2P; FIG. 19B depicts the trace of the library prep constructed from the saliva sample of donor A treated with Oragene/STAT; FIG. 19C depicts the trace of the library prep constructed from the saliva sample of donor B purified with Oragene/prepIT·L2P; and FIG. 19D depicts the Bioanalyzer gel trace of the library prep constructed from the saliva sample of donor B treated with Oragene/STAT.

DETAILED DESCRIPTION

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

The present application provides a system, method, composition and kit for removing a detergent (such as, for example, an anionic detergent or anionic surfactant) from an aqueous solution. The system, method, composition and kit may also be used for removing detergent-associated and/or detergent-bound molecules from the aqueous solution, if present. The present system and method effectively remove the detergent, and any detergent-associated/detergent-bound molecules present, to barely detectable levels by sequestering the detergent and detergent-associated/detergent-bound molecules, such as protein, into an organic layer. The result of mixing the aqueous solution with the composition is a two phase mixture comprising an upper aqueous phase substantially free of the detergent and any detergent-associated/detergent-bound molecules that may be present, and a lower, denser organic phase comprising the detergent, and any detergent-associated/detergent-bound molecules that may be present. The detergent removal composition consists of the following components: 1) a salt; 2) a water immiscible alcohol; and 3) a halocarbon.

As used herein, a detergent removal composition, detergent removal system, detergent removal method, and detergent removal kit, refer to compositions, systems, methods and kits for the removal of a detergent and, if present, detergent-associated and/or detergent-bound molecules, from an aqueous solution. In certain embodiments, the detergent is an anionic detergent.

As would be understood by a worker skilled in the art, when the detergent, and detergent-associated/detergent-bound molecules present, are described herein as being "removed" from the aqueous solution, it is likely that some low concentration of detergent or detergent-associated/detergent-bound molecules remains in the aqueous solution. However, to be considered "removed", the detergent and detergent-associated/detergent-bound molecule concentration in the aqueous solution will have dropped below a threshold detergent concentration selected based on the ultimate application of the aqueous solution. In one embodiment, following "removal" of the detergent (and detergent-associated/detergent-bound molecules, if present) using the present system, composition, method and kit, the concentration of detergent (and detergent-associated/detergent-bound molecules, if present) in the aqueous solution is below a detectable concentration using the Stains-All Assay described in Example 1.

In certain embodiments, a "detergent", as used herein, includes detergents which include, but are not limited to, an anionic detergent, for example. Non-limiting examples of anionic detergents that can be removed from an aqueous solution using the present detergent removal system, method, composition, and kit are sodium dodecyl sulfate (SDS) and Sarkosyl.

Detergent Removal Composition and System

As noted above, the detergent removal composition and system described herein contain at least three components: a salt; a water immiscible alcohol; and a halocarbon. These components can be maintained separately until they are mixed with the aqueous solution for detergent removal, or they can be combined and stored together as a mixture of all three components, or any two of the three components, prior to being used in removing detergent (and detergent-associated/detergent-bound molecules, if present) from an aqueous solution. As such, the present detergent removal system can further comprise one or more containers for storing the salt; water immiscible alcohol; and halocarbon components prior to use.

The present composition and system may, thus, ideally be used to remove inhibitors from aqueous solutions, i.e., inhibitors that inhibit reactions such as downstream applications, including, but not limited to, PCR (including RT-PCR), library preparation, and nucleotide sequencing. Inhibitors may include, for example, enzymatic inhibitors, i.e., inhibitors of enzyme-dependent reactions in subsequent applications, for example.

In certain embodiments, at least a portion of the aqueous phase (i.e., the phase that does not substantially contain the detergent, and detergent-associated or detergent-bound molecules, if present) may be used directly for downstream applications including, but not limited to, PCR (including RT-PCR), library preparation, and nucleotide sequencing, Salt Component Salts useful in the present system, composition and method are quaternary ammonium salts or alkali metal salts. Specific examples of salts that can be used in the present system, composition and method include, but are not limited to, ammonium acetate, ammonium chloride, ammonium sulfate, a betaine salt, choline chloride, diethylamine hydrochloride, dimethylethanolamine, ethanolamine, ethylammonium chloride, methylammonium chloride, tetra-n-butylammonium acetate, tetraethylammonium chloride monohydrate, tetramethylammonium chloride, tetra-n-propylammonium chloride, methyltri-n-butylammonium chloride, triethylamine hydrochloride, triethylmethylammonium chloride, trimethylamine hydrochloride, an acid salt of 1-butylamine, an acid salt of 1-pentylamine, an acid salt of 1-hexylamine, an acid salt of 1-dodecylamine, lithium chloride; sodium chloride, potassium chloride, and combinations thereof.

Alcohol Component

The present system and method takes advantage of the change in solubility characteristic of the detergent, such as an anionic detergent, when an aqueous solution comprising the detergent is mixed with the present detergent removal composition. In order to facilitate the formation of a two-phase mixture, the alcohol component must be immiscible or only sparingly miscible in water. The water immiscible alcohol has the structure of Formula I $$R^1\text{—OH} \qquad\qquad\qquad\qquad\qquad\qquad\text{I}$$

where $R^1$ is an optionally substituted, linear, branched or cyclic $C_4$-$C_{12}$ alkyl.

Examples of water immiscible alcohols useful in the present systems, methods and compositions for detergent removal include, but are not limited to, 1-butanol, 3-methyl-1-butanol, 2-butanol, 1-heptanol, 1,2-hexanediol, 1-hexanol, 2-nonanol, 1-pentanol, 4-methyl-2-pentanol, cyclopentanol, 1-propanol, 1-undecanol or combinations thereof.

Halocarbon Component

One of the functions of the halocarbon component is to increase the density of the organic phase in the two phase mixture that forms on mixing an aqueous solution with the present detergent removal composition, such that the organic phase is the bottom phase and the aqueous phase is the upper phase. Furthermore, to ensure good separation of the two phases, the halocarbon must be immiscible or only sparingly miscible with water and must be miscible with the alcohol component.

Examples of halocarbons that are useful in the present systems, methods and compositions for detergent removal include, but are not limited to, 1-bromo-3-chloropropane, 1-bromo-6-chlorohexane, bromodichloromethane (BDCM), chlorodibromomethane, chloroform, 2-iodopropane, (poly)chlorotrifluoroethylene (—(CF$_2$CFCl)$_n$— where n=2 to 10; specifically the halocarbon oil 6.3 obtained from Halocarbon Products Corporation, River Edge, NJ; CAS #9002-83-9), or a combination thereof. Perfluorononane is an example of a halocarbon that did not function well in the present detergent removal composition. Without wishing to be bound by theory, this is likely due to the fact that the perfluorononane was not miscible with the alcohol component.

Optional Components

The present system and composition can optionally contain additional components depending on, for example, the nature of the aqueous solution containing the detergent to be removed, or the ultimate application of the aqueous solution following detergent removal (and removal of detergent-associated or detergent-bound molecules, if present).

In one embodiment, the detergent removal system additionally comprises glass beads, which can function to improve and/or speed up the lysis of cells present in the aqueous sample or improve mixing of the aqueous solution comprising the detergent with the salt, alcohol and halocarbon components. Without being limited by theory it is believed that when a raw sample (e.g. saliva) is vigorously mixed concurrently with SDS and the composition of the present invention, the beads help to homogenize the sample, lyse the cells and bring SDS into contact with protein-bound DNA. SDS then strips the protein from the DNA and the composition segregates the SDS and SDS-associated/SDS-bound molecules to the organic phase.

In another embodiment, the detergent removal system additionally comprises a reducing agent. A reducing agent can also be present in, or added to, the aqueous solution containing the detergent to be removed, before mixture with the present detergent removal composition. Such a reducing agent can be, for example, dithiothreitol (DTT), mercaptohexanol, mercaptoundecanol, dimercaptopropanol or mercaptobutanol.

In yet another embodiment, the detergent removal system additionally comprises a chelator and/or a buffer. A chelator and/or a buffer can also be present in, or added to, the aqueous solution containing the detergent to be removed, before mixture with the present detergent removal composition. Such a chelator agent can be, for example, ethylene glycol tetraacetic acid (EGTA), (2-Hydroxyethyl)ethylenediaminetriacetic acid (HEDTA), diethylene triamine pentaacetic acid (DTPA), NitriloTriAcetic Acid (NTA), ethylenediaminetriacetic acid (EDTA), cyclohexanediaminetetraacetic acid (CDTA), citrate anhydrous, sodium citrate, calcium citrate, ammonium citrate, ammonium bicitrate, citric acid, diammonium citrate, ferric ammonium citrate, lithium citrate, or any combination thereof. Any suitable buffer may be used and are well known to those in the art.

In another embodiment, the detergent removal system additionally comprises a lipophilic stain, such as Nile Red. Nile Red stains intracellular lipid, cell membranes and hydrophobic protein surfaces. When mixed with a biological sample and the present composition the stain partitions exclusively to the lower organic phase, leaving the upper aqueous phase clear and colourless. Such a lipophilic stain can be, for example, 9-Anthryldiazomethane, Fluorol Yellow 088, N,N,N-Trimethyl-4-(6-phenyl-1,3,5-hexatrien-1-yl) phenylammonium p-toluenesulfonate (TMA-DPH), 3,3'-Dioctadecyloxacarbocyanine percholorate, 1,6-Diphenyl-1,3,5-hexatriene, Sudan III, Sudan Orange G, Nile Blue chloride and Solvent Blue 37.

Method of Detergent Removal

The present application provides a method of removing a detergent from an aqueous solution. In certain embodiments, the detergent is an anionic detergent. In certain embodiments, the anionic detergent is SDS or Sarkosyl. The present method may also be used to remove detergent-associated or detergent-bound molecules that may be present in the aqueous solution. The present method may, thus, ideally be used to remove inhibitors from aqueous solutions, i.e. inhibitors that inhibit reactions such as downstream applications, including, but not limited to, PCR (including RT-PCR), library preparation, and nucleotide sequencing. Inhibitors may include, for example, enzymatic inhibitors, e.g., inhibitors of enzyme-dependent reactions in subsequent applications, for example.

Simply, the method comprises mixing an aqueous solution comprising the detergent to be removed, with a salt, a water immiscible alcohol, and a halocarbon. The three components can be mixed with the aqueous solution in a single step or in multiple steps. The order of addition is not important; rather it is important that the components of the detergent removal composition are well mixed with the aqueous solution. This mixing step can include mechanical agitation, such as vortexing, to improve or facilitate mixing.

The aqueous solution can be any aqueous solution that contains a detergent to be removed. In certain embodiments, the detergent is an anionic detergent. In certain embodiments, the detergent is SDS or Sarkosyl. The aqueous solution may also contain detergent-associated and/or detergent-bound molecules. Such a solution can be, for example, a biological sample, such as saliva, sputum, buccal swab sample, serum, plasma, blood, pharyngeal, nasal/nasal pharyngeal or sinus swabs or secretions, throat swabs or scrapings, urine, mucous, feces, chyme, vomit, gastric juices, pancreatic juices, gastrointestinal juices, semen/sperm, cerebral spinal fluid, products of lactation or menstruation, egg yolk, amniotic fluid, aqueous humour, vitreous humour, cervical secretions or swabs, vaginal fluid/secretions/swabs or scrapings, bone marrow aspirates, pleural fluid, sweat, pus, tears, lymph, bronchial or lung lavage or aspirates, cell cultures and cell suspensions, connective tissue, epithelium, mucosal membrane, muscle tissue, placental tissue, organ tissue, nerve tissue, hair, skin, nails, plants, plant extracts, algae, microorganisms, soil samples, sewage, wastewater, foodstuff, or the like.

When the sample includes cells or tissue, it is beneficial to ensure good mixing with the detergent removal composition in order to maximize detergent removal. In one embodiment, glass beads or other mechanical means are added before or during mixing to facilitate sample dispersion and cell lysis. Alternatively, a tissue sample may be homogenized by mechanical or chemical means or digested with enzymes (e.g. Proteinase K) before or after mixing with SDS and the detergent removal composition. Alternatively, SDS alone may be able to lyse sufficient number of cells covering the surface of a solid piece of tissue (e.g. muscle biopsy or tumour biopsy), releasing nucleic acids into solution, subsequently treated with the detergent removal composition and used in downstream applications.

The biological samples may or may not also contain microorganisms, such as viruses, bacteria, yeast, fungi, archaea, and protists.

After full mixing of the aqueous solution with the detergent removal composition the resulting mixture is allowed to settle or is briefly centrifuged to form two phases. The detergent (and any detergent-associated or detergent-bound molecules) will be partitioned in the lower organic phase leaving the upper aqueous phase substantially free of the detergent. The top aqueous phase can be readily isolated by standard means, such as decanting or pipetting for downstream analysis without contamination from the lower organic phase.

This method is not only effective in removing a detergent, such as an anionic detergent, from the aqueous solution, but also in removing detergent-associated, or -bound, molecules and macromolecules. In a specific embodiment, the detergent-associated or -bound molecules are proteins. Anionic detergents, such as SDS, are known to lyse cells in a biological sample by disrupting the membrane lipid bilayer and denaturing proteins. Since SDS effectively solubilizes and binds tightly to proteins, it is believed the present detergent removal method and system can readily remove and isolate both the detergent and the detergent-associated/bound proteins into the lower organic phase. Accordingly, the present application further provides a method of extracting proteins from an aqueous solution, such as a biological sample. Thus, the method, composition, system and kit as described herein may ideally be used to remove inhibitors from aqueous solutions, i.e., inhibitors that inhibit reactions such as downstream applications including, but not limited to, PCR (including RT-PCR), library preparation, and nucleotide sequencing. Inhibitors may include, for example, enzymatic inhibitors, e.g., inhibitors of enzyme-dependent reactions in subsequent applications, for example.

At least a portion of the aqueous phase (i.e., the phase that does not substantially contain the detergent, and detergent-associated or detergent-bound molecules, if present) may then be used directly for downstream applications including, but not limited to, PCR (including RT-PCR), library preparation, and nucleotide sequencing.

Also provided herein are kits for detergent removal. The kits include the salt, alcohol and halocarbon components of the detergent removal composition, in a single container or in two or three separate containers. Optionally the kit also includes instructions for performing the present detergent removal method and/or a sample collection container and/or a sample collection container containing a detergent solution. As stated above, in certain embodiments, the kit may also be used to remove detergent-associated and/or detergent-bound molecules from the aqueous solution that may be present.

To gain a better understanding of the invention described herein, the following examples are set forth. It should be understood that these examples are for illustrative purposes only. Therefore, they should not limit the scope of this invention in any way.

EXAMPLES

Example 1: Sensitive Assay System for Detecting Low Concentrations of SDS

A sensitive assay system was developed to quantify very small (<0.01% wt/vol) amounts of SDS in samples. The quantification of SDS in this assay is based on the use of the 3,3'-diethyl-9-methyl-4,5,4',5'-dibenzothiacarbocyanine dye, also known as Stains-All. This is a fuchsia dye that turns yellow in the presence of SDS. The assay allows for the accurate detection and quantification of as little as 0.003% SDS in a sample.

The assay was adapted from the one described by Rusconi et al. in "Quantification of Sodium Dodecyl Sulfate in Microliter-Volume Biochemical Samples by Visible Light Spectroscopy." *Analytical Biochemistry*. 2001. 295, 31-37.

Equipment
Tecan Infinite 200 Plate Reader
Grenier 96 well Flat Bottom Transparent Polystyrol Plate
Reagents
Stains-All [Sigma-Aldrich, Cat. No. E9379-1G]
Isopropanol [EMD, Cat. No. PX1834-6]
DMSO [BDH, Cat. No. B10323]
10% SDS (w/v) [EMD. Cat. No. DX2490-2]
  Diluted to 1% in $H_2O$ prior to carrying out the assay Preparation of Solutions Stains-All Stock Solution (1.8 mM) comprised of 1 mg/mL in 50% (v/v) isopropanol. This stock solution is stable at 4° C. for 1 month in the dark.
Stains-All Intermediate Solution (90 µM):
  The intermediate solution was prepared by mixing 1 mL Stains-All Stock Solution (1.8 mM) with 1 mL DMSO and 18 mL $H_2O$. This Stains-All Intermediate Solution is stable for 3 days when stored at room temperature in the dark.
Preparation of SDS Standard Curve: The standard curve was prepared using the following standard solutions:
  a. 0.05% SDS=5 µl 1% SDS+95 µl $H_2O$
  b. 0.025% SDS=50 µl (A)+50 µl $H_2O$
  c. 0.0125% SDS=50 µl (B)+50 µl $H_2O$
  d. 0.00625% SDS=50 µl (C)+50 µl $H_2O$
  e. 0.003125% SDS=50 µl (D)+50 µl $H_2O$
  f. 0.0015625% SDS=50 µl (E)+50 µl $H_2O$
  g. 0.00078125% SDS=50 µl (F)+50 µl $H_2O$
  h. 0% SDS=$H_2O$ Procedure
1. Transfer 5 µl of either SDS standard solution or a sample to a well of a 96 well plate
2. Add 195 µl of Stains-All Intermediate Solution to each sample immediately before reading absorbance (Note: Stains-All is light sensitive).
3. Read absorbance from 420 nm-480 nm using a standard plate reader.
4. Calculate absorbance 'Area Under the Curve' (AUC) (420-480 nm) using GraphPad Prism 5 software.

The standard curve (represented by the dark bars on the graphs) was prepared by plotting the AUC against the known SDS concentrations. The concentration of SDS in unknown samples was then readily obtained using the calculated AUC and the standard curve. Unless otherwise indicated, this method was used in determining SDS concentration in the following Examples.

Example 2: Comparison of Detergent Removal Compositions

Figure 1:
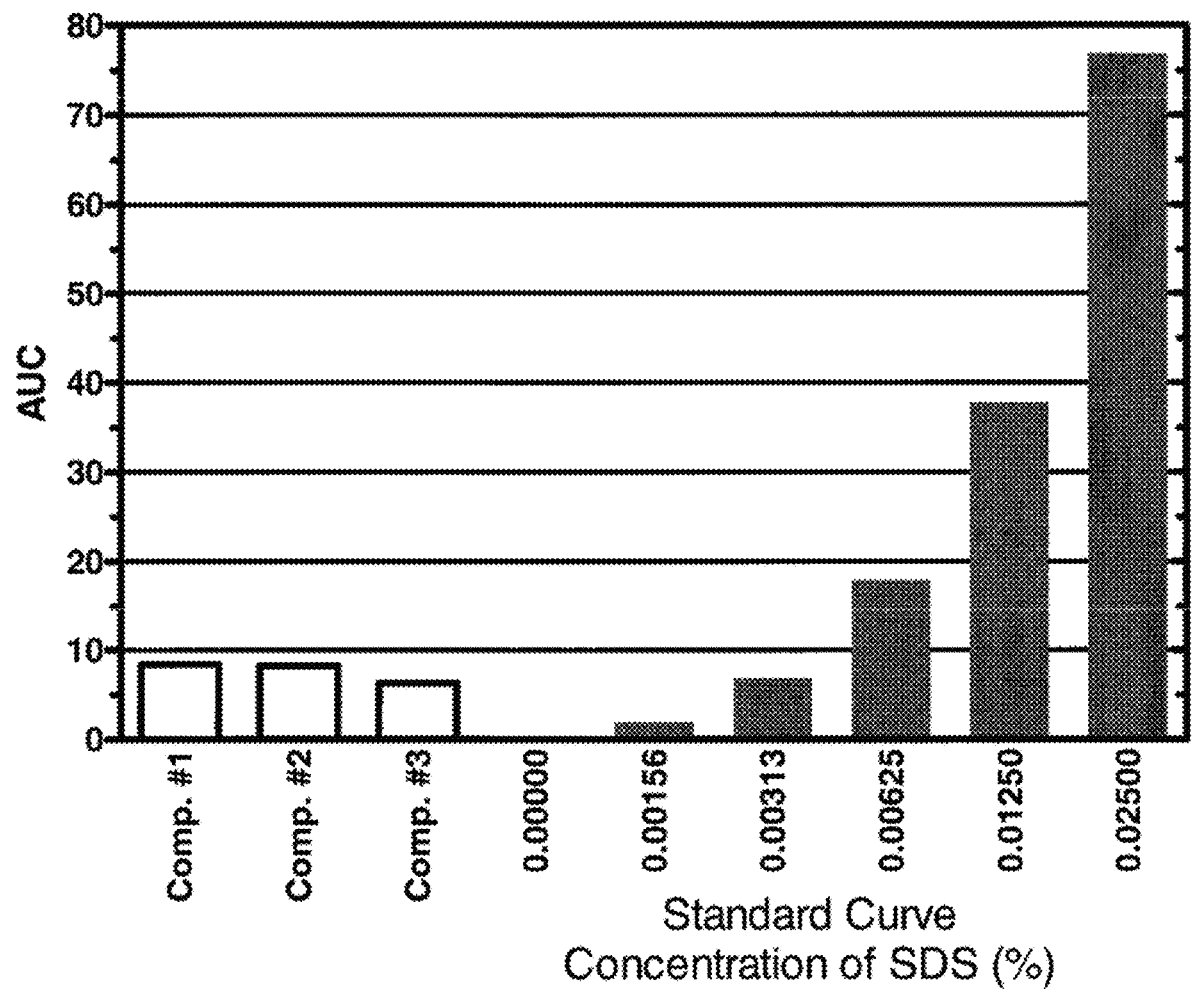
FIG. 1 depicts the treatment of 1% SDS in water solution with a detergent removal composition; composition 1 comprises a 1:1 mix of 1-pentanol and bromodichloromethane (BDCM) with 150 mM ammonium chloride ($NH_4Cl$); composition 2 comprises a 1:1 mix of 1-pentanol and chloroform with 150 mM $NH_4Cl$; composition 3 comprises a 1:1 mix of 1-pentanol and 2-iodopropane with 150 mM $NH_4Cl$.
Figure 2:
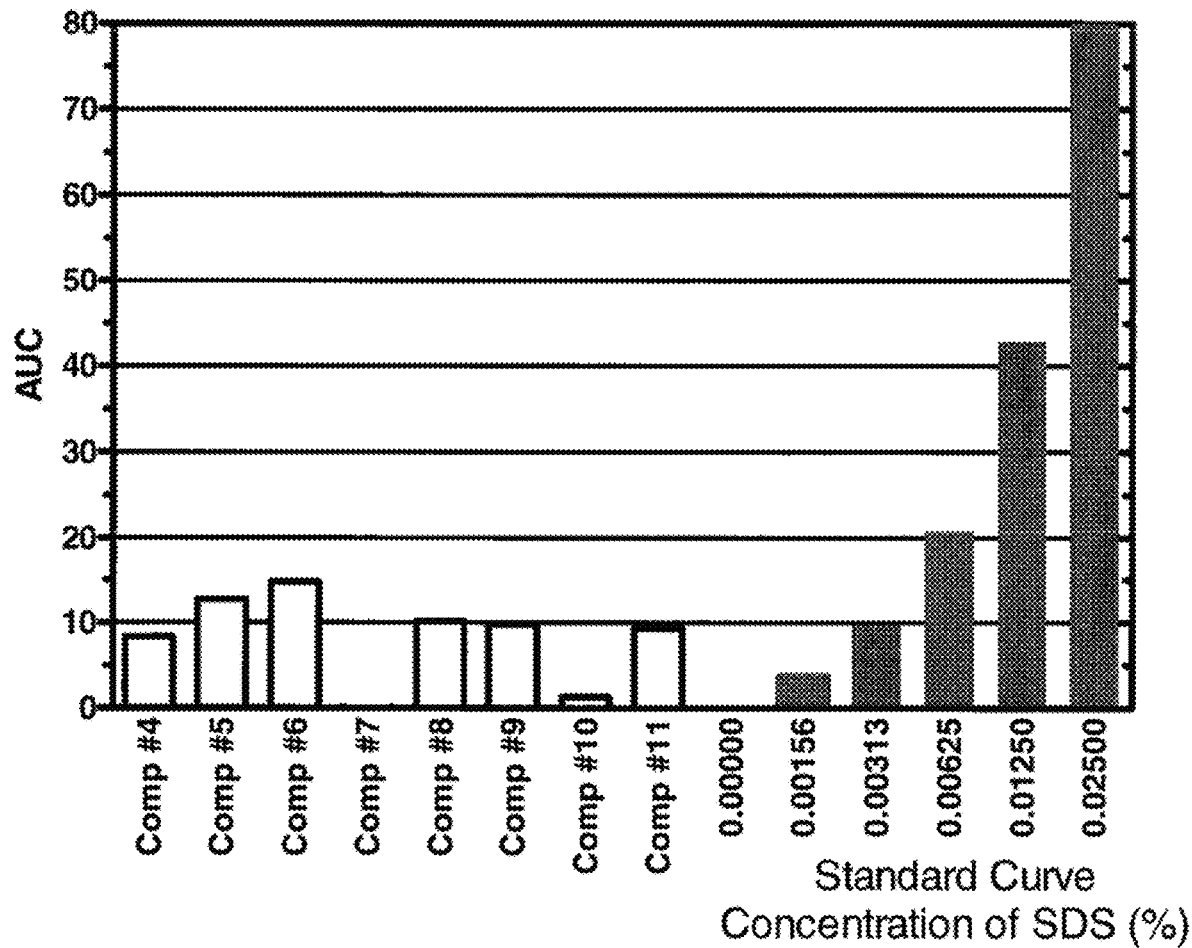
FIG. 2 depicts the treatment of 4% SDS in water solution with a detergent removal composition; all the compositions studied comprise a 1:1 mix of 1-pentanol and BDCM with a salt as follows: Composition 4: 175 mM of $NH_4Cl$, Composition 5: 200 mM of $NH_4Cl$; Composition 6: 125 mM of methyltri-n-butylammonium chloride; Composition 7: 150 mM of methyltri-n-butylammonium chloride; Composition 8: 150 mM of triethylamine hydrochloride; Composition 9: 175 mM of triethylamine hydrochloride; Composition 10: 175 mM of tetra-n-butylammonium acetate; Composition 11: 200 mM of tetra-n-propylammonium chloride.
Figure 3:
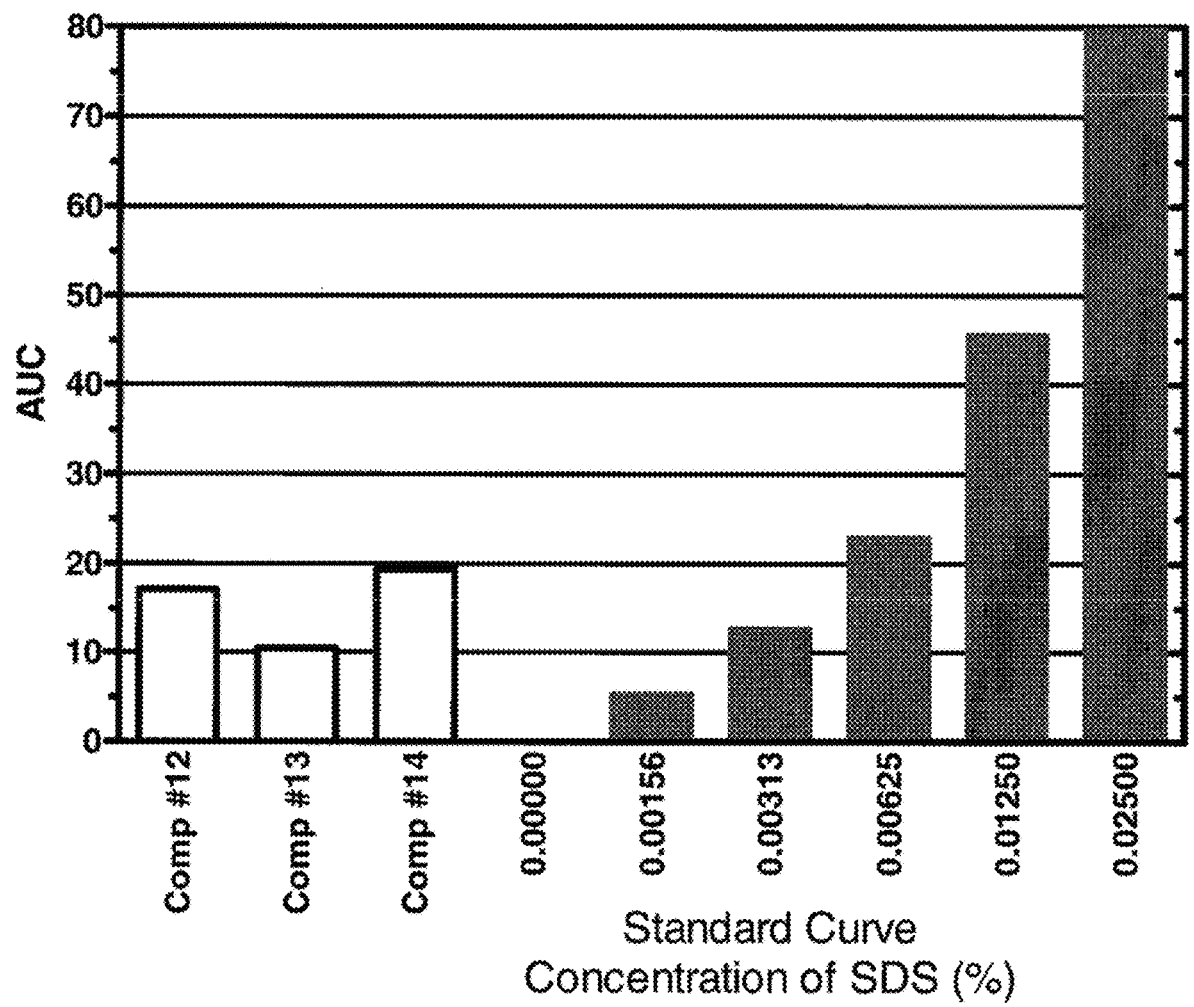
FIG. 3 depicts the treatment of 10% SDS in water solution with a detergent removal composition; all the compositions studied comprise a 1:1 mix of 1-pentanol and BDCM with varying concentrations of $NH_4Cl$ as follows: Composition 12: 275 mM; Composition 13: 300 mM; and Composition 14: 325 mM and the resulting data demonstrates that, even at a starting concentration of 10%, the SDS could be reduced to <0.00625% in one step with $\frac{1}{5}^{th}$ volume of the composition.

Various detergent removal compositions of the present invention were used to remove SDS from aqueous solutions containing known amounts of SDS. One hundred microlitre aliquots of the aqueous compositions containing different concentrations of SDS were prepared. SDS removal was carried out by adding a salt and 20 µl of a 1:1 (vol/vol) mixture of a higher alcohol and halocarbon as described below. The tubes were vortexed vigorously for 2 minutes and centrifuged at 13,000 rpm for 2 minutes. The top (aqueous) phase was removed and residual SDS in the aqueous phase was quantified using the modified Stains-All Assay described in Example 1. The results are shown in FIGS. 1 to 3. The dark bars represent the SDS standard solutions, whereas white bars represent results from the tested detergent removal compositions.

The graph shown in FIG. 1 depicts the results of an experiment in which an aqueous solution comprising 1% SDS was treated with various detergent removal compositions. Composition 1 comprises a 1:1 mix of 1-pentanol and bromodichloromethane (BDCM) with 150 mM ammonium chloride ($NH_4Cl$). Composition 2 comprises a 1:1 mix of 1-pentanol and chloroform with 150 mM $NH_4Cl$. Composition 3 comprises a 1:1 mix of 1-pentanol and 2-iodopropane with 150 mM $NH_4Cl$. In each case, the amount of SDS detected in the aqueous phase following treatment was less than 0.00625% and, when the halocarbon used was 2-iodopropane, the amount of SDS detected following detergent removal was less than 0.003125%. This demonstrates a remarkably efficient (>99.7%) extraction of SDS from the aqueous phase in a single treatment using only one-fifth volume of the detergent removal composition.

The graph shown in FIG. 2 depicts the results of an experiment in which an aqueous solution comprising 4% SDS was treated with various detergent removal compositions. In this study all compositions comprised a 1:1 mix of 1-pentanol and BDCM with a salt as follows: Composition 4: 175 mM of $NH_4Cl$, Composition 5: 200 mM of $NH_4Cl$; Composition 6: 125 mM of methyltri-n-butylammonium chloride; Composition 7: 150 mM of methyltri-n-butylammonium chloride; Composition 8: 150 mM of triethylamine hydrochloride; Composition 9: 175 mM of triethylamine hydrochloride; Composition 10: 175 mM of tetra-n-butylammonium acetate; Composition 11: 200 mM of tetra-n-propylammonium chloride. In each case, the amount of SDS detected in the aqueous phase following treatment was less than 0.00625%. Again, the results demonstrate a remarkably efficient (up to >99.9%) extraction of SDS from the aqueous phase in a single treatment using only one-fifth volume of the detergent removal composition.

The graph shown in FIG. 3 depicts the results of an experiment in which an aqueous solution comprising 10% SDS was treated with various detergent removal compositions. In this study all compositions comprise a 1:1 mix of 1-pentanol and BDCM with varying concentrations of $NH_4Cl$ as follows: Composition 12: 275 mM; Composition 13: 300 mM; and Composition 14: 325 mM. In each case, the amount of SDS detected in the aqueous phase following treatment was less than 0.00625%. Once again, the results demonstrated a highly efficient (up to >99.9%) extraction of SDS from the aqueous component in a single treatment using only one-fifth volume of the detergent removal reagent, even at a very high (10% wt/vol) initial SDS concentration.

Example 3: Removal of SDS from a Saliva-Containing Sample

To demonstrate the effectiveness of the present invention in an aqueous composition containing a biological sample, a fresh human saliva sample was collected in a 15 ml conical tube. One milliliter of saliva was treated with an equal volume of lysis buffer containing 4% SDS and 250 mM LiCl and digested with Proteinase K ("PK") at 60° C. for 15 minutes. PK was inactivated by heating at 90° C. for 15 minutes and a 93.75 µl aliquot of the treated saliva in lysis buffer was mixed with 6.25 µl of a 2 M ammonium chloride solution.

Figure 4:
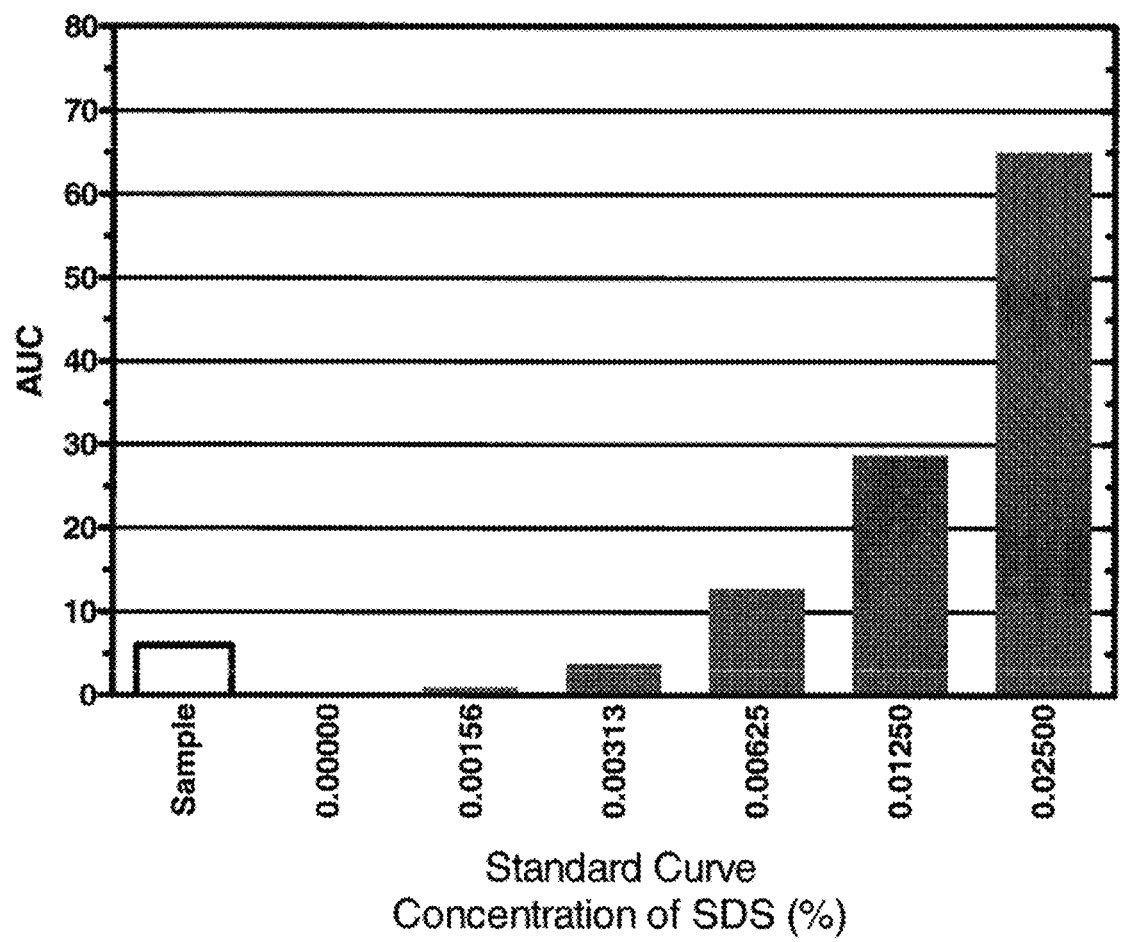
FIG. 4 depicts the treatment of a saliva sample collected into an aqueous solution comprising 2% SDS with a detergent removal composition; the composition used comprised a 1:1 mix of 1-pentanol and BDCM with 125 mM ammonium chloride, which demonstrated efficient removal of SDS even in the presence of this biological sample.

Detergent removal was carried out by adding 20 µl of a 1:1 mixture of 1-pentanol and BDCM to 100 µl of the treated saliva sample. The tube was vortexed vigorously for 2 minutes and centrifuged at 13,000 rpm for 2 minutes. The top (aqueous) phase was removed and SDS was quantified using the modified Stains-All Assay described in Example 1. The results are shown in FIG. 4. These results demonstrate the successful removal of >99.7% of the SDS from a saliva-containing aqueous sample using the composition and procedure described herein.

Example 4: Removal of SDS from a Venous Blood-Derived Sample

To demonstrate the effectiveness of the present invention in an aqueous composition containing a complex biological sample, human venous blood was collected in EDTA tubes. One millilitre of blood was lysed in three volumes of a lysis buffer containing SDS and ammonium chloride at 70° C. for 15 minutes. The final concentrations of SDS and ammonium chloride in the lysed blood sample were 2.5% and 175 mM, respectively.

Figure 5:
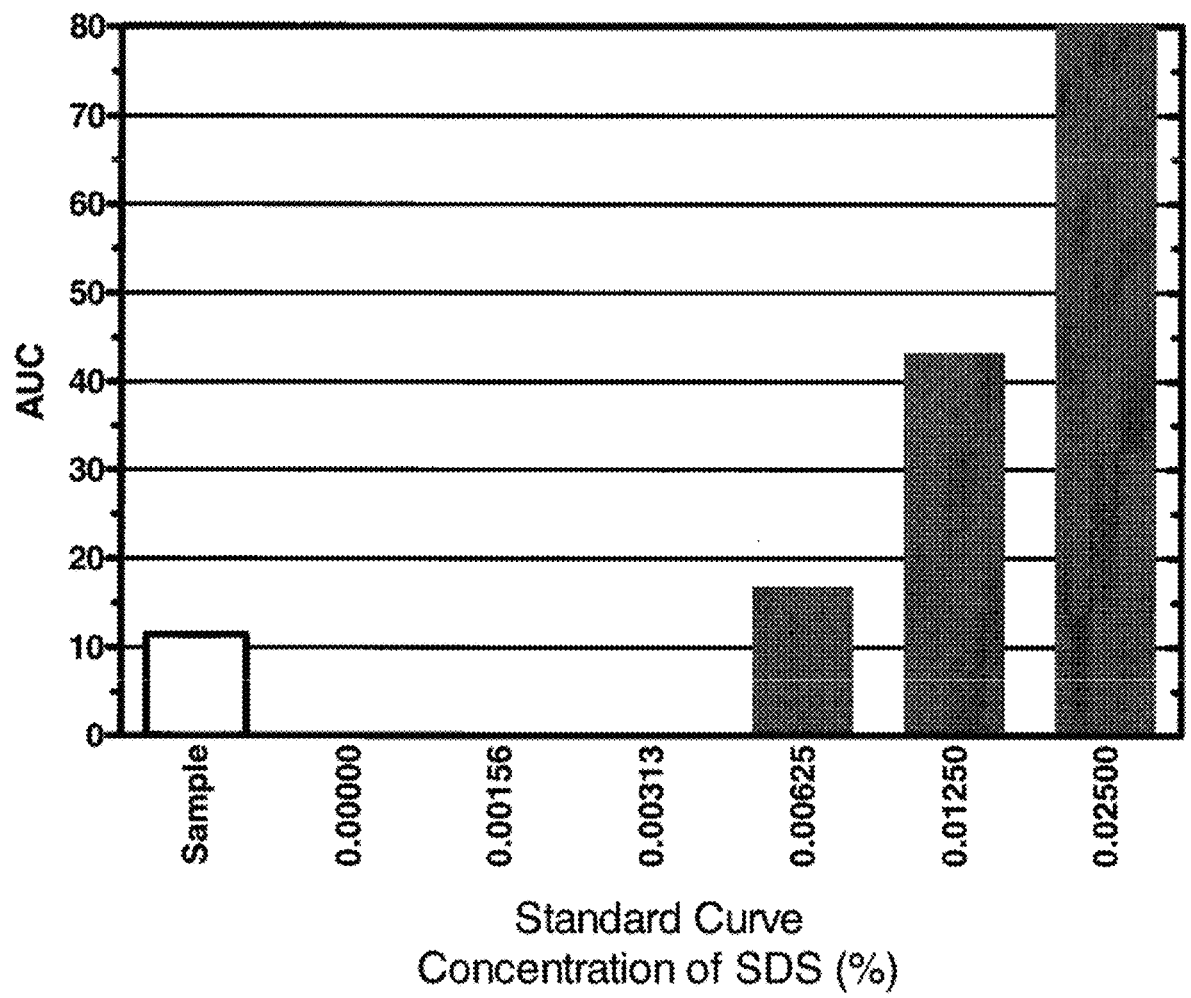
FIG. 5 depicts the treatment of a blood sample collected into an aqueous solution comprising 2.5% SDS with a detergent removal composition; the composition used comprised a 1:1 mix of 1-pentanol and BDCM with 175 mM ammonium chloride and the results showed that SDS was efficiently removed even in the presence of this complex biological sample.

Detergent removal was carried out on 100 µl of lysed blood sample by adding 20 µl of a 1:1 mixture of pentanol and BDCM. The tubes were vortexed vigorously for 2 minutes and centrifuged at 13,000 rpm for 2 minutes. The top (aqueous) phase was removed and SDS was quantified using the modified Stains-All Assay described in Example 1. The results, shown in FIG. 5, demonstrated that SDS can be successfully removed (>99%), even from a complex biological sample such as venous blood.

Example 5: Inhibition of PCR by Various Concentrations of SDS

Multiple qPCR reactions were carried out using the following master mix: 2.5 µl of 1mg/ml bovine serum albumin (BSA), 2.5 µl of 10×PCR Buffer, 1.5 µl of 50 mM $MgCl_2$, 0.5 µl of 10 mM dNTPs, 0.5 µl of 10 pMol forward primer, 0.5 µl of 10 pMol reverse primer (human 18S-165 forward 5' gtggagcgatttgtctggtt and human 18S-165 reverse 5' ggacatctaagggcatcacag) 0.5 µl of 0.5 µM Syto 9, 0.2 µl of 5 U/µl Taq Polymerase, 12.3 µl of water.

qPCR reactions with known amounts of control DNA and varying concentrations of SDS ranging from 1% to 0.001% wt/vol were carried out using the 18S rRNA gene, a 57.4° C. primer annealing temp and 30 cycles.

Figure 6:
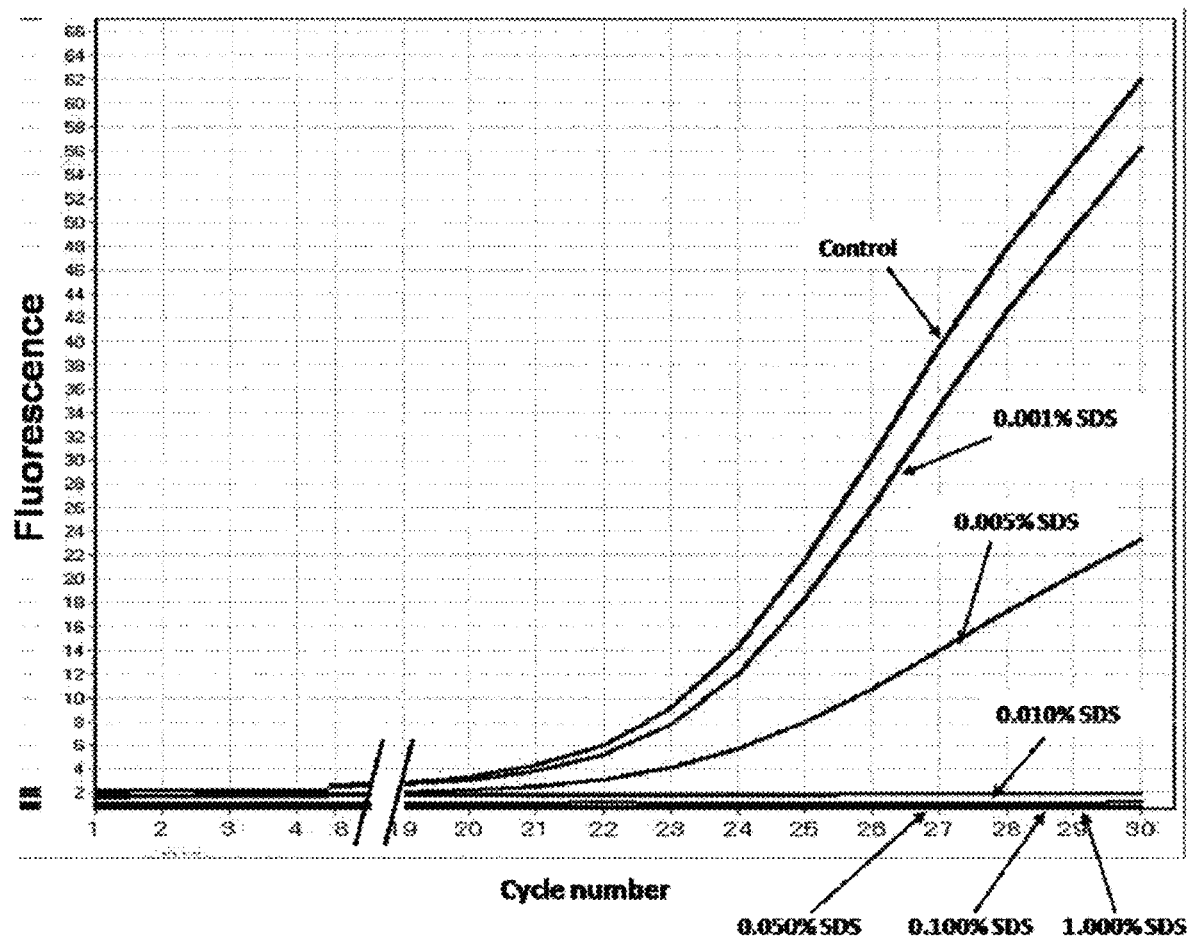
FIG. 6 depicts the results of qPCR carried out on aqueous solutions of known SDS concentrations: a control containing no SDS, and solutions of 0.001% SDS, 0.005% SDS, 0.01% SDS, 0.05% SDS; 0.1% SDS and 1% SDS were tested and compared and the results demonstrated that partial inhibition of qPCR occurred in the presence of 0.005% SDS and complete inhibition occurred when SDS was present at 0.01%.

Results are presented in FIG. 6 demonstrating that qPCR was completely inhibited at concentrations of SDS as low as 0.01% with partial inhibition observable at 0.005%. These ranges are in agreement with the published data referred to above.

Figure 7:
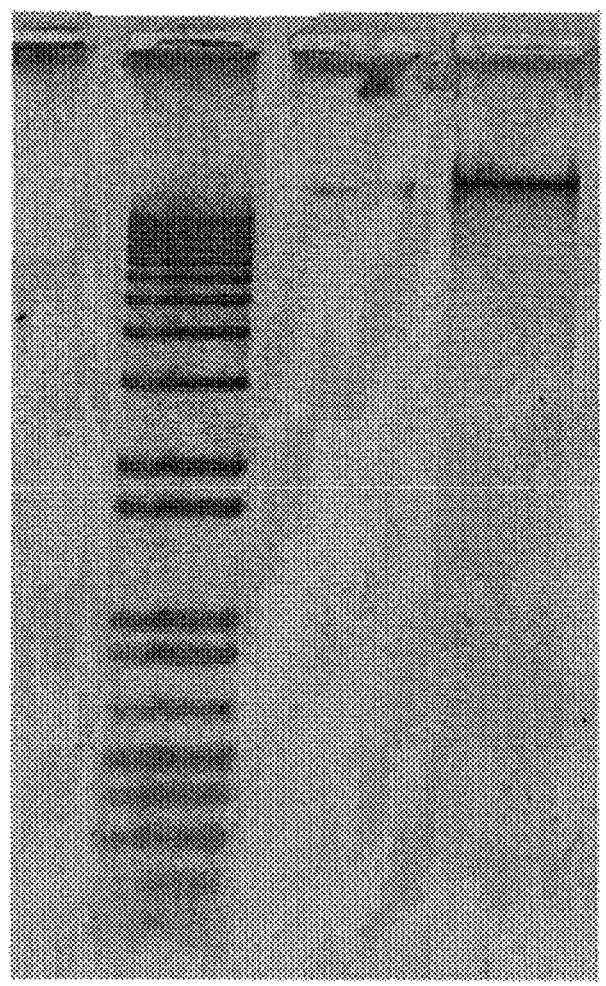
FIG. 7 is a photograph of an agarose gel stained with SybrGold™ (Invitrogen) following electrophoresis of an aliquot of the aqueous phase from a saliva sample collected into a detergent solution and treated with a detergent removal composition as described herein; high molecular weight DNA can be seen in the sample lane alongside a 1

Example 6: Use of DNA in Biological Samples for qPCR Following Detergent Removal Saliva-Derived Sample The aqueous phase of a lysed saliva sample was obtained after treatment with the detergent removal compositions, as described in Example 3. A 12 µl aliquot of the aqueous phase was electrophoresed in a 1% agarose gel alongside a 1 Kb+ DNA ladder; the gel was then stained with SybrGold™ (Invitrogen, Cat # S11494). Results are presented in FIG. 7 where high molecular weight DNA (>23 Kb) can be seen, thus demonstrating that treatment with the composition of the present invention leaves the DNA intact and in the aqueous phase.

qPCR was performed using an aliquot of the aqueous phase following detergent removal according to the method described in Example 5 above. Data for 4 µl of saliva-derived aqueous phase directly added to total of 25 µl of the qPCR reaction is shown in FIG. 8. For comparison, 5 ng and 50 ng of purified DNA was also subjected to qPCR for the 18S rRNA gene.

These results provided further demonstration that SDS could be efficiently and rapidly removed from a saliva-derived aqueous sample, following the detergent removal procedure described above. The data obtained in FIG. 8, showing successful qPCR implies that the saliva-derived aqueous phase contains only very low amounts of residual PCR inhibitors. Possibly, the use of a smaller aliquot in a larger volume of qPCR mixture could give similar results. In fact, dilution is a common approach to dealing with inhibitors naturally present in blood samples. However, this approach would result in a loss of total DNA obtainable from a sample and would introduce more sources of error in the experimental method. It is always preferable to have the ability to use larger and more concentrated samples. The presently described method and composition allows the use of samples without the need to use a high dilution approach.

Blood-Derived Sample

The aqueous phase for this example was obtained after detergent removal from a lysed blood sample as described in Example 4. An 8 µl aliquot of the aqueous phase following detergent removal was electrophoresed in a 0.8% agarose gel alongside a 1 Kb+ DNA ladder, following which the gel was stained with ethidium bromide. Results are presented in FIG. 9 where high molecular weight DNA (>23 Kb) can be seen, thus demonstrating that treatment with the composition of the present invention leaves the DNA intact and in the aqueous phase.

qPCR as described in Example 5 above was performed using an aliquot of the aqueous phase following detergent removal. Data for both a 2 µl and a 4 µl of blood-derived aqueous phase directly added to give a total of 25 µl of qPCR reaction is shown in FIG. 10.

These results provided further demonstration that SDS was effectively removed from the blood-derived aqueous sample, following the detergent removal procedure described above. Since blood is known to contain significant amounts of PCR inhibitors, the data of FIG. 10 is quite remarkable in that high dilution of the sample was not required once the SDS-containing blood sample was treated with the detergent removal composition as described in Example 4. As is demonstrated below, not only was SDS removed from the sample, but any SDS-associated protein was also removed and may potentially explain this remarkable result.

Example 7: Use of RNA from Biological Samples for Reverse Transcriptase (RT)-PCR Following Detergent Removal Saliva Two mL of a fresh saliva sample was collected in a 15 ml conical tube and mixed with an equal volume of a lysis buffer (4% SDS, 250 mM LiCl).

A 200 µl aliquot of the lysed saliva was mixed with PK and incubated at 60° C. for 15 minutes. The PK was then inactivated by heating at 90° C. for 15 minutes. 10 µl of 2 M ammonium chloride and 40 µl of a 1:0.8 (vol/vol) mixture of 1-pentanol and (poly)chlorotrifluoroethylene were added. The tube was vortexed vigorously for 2 minutes and centrifuged at 13,000 rpm for 2 minutes. The top (aqueous) phase was removed and electrophoresed in 1% agarose gel. The gel was treated with SybrGold to stain the nucleic acids (FIG. 11). Bacterial 16S and 23S ribosomal RNA bands were seen demonstrating that the detergent removal composition described herein left RNA intact in the aqueous phase. No human 28S and 18S ribosomal RNA bands were seen because they are present in very small amounts in saliva, too low to be detected by staining with SybrGold. However, human ribosomal RNA can be detected by RT-PCR, as shown in the next section.

The aqueous phase derived from a saliva sample was treated as described above, except that a 1:1 (vol/vol) mixture of BDCM and 1-pentanol was used as a detergent removal composition. One µl of saliva aqueous phase was directly added to 20 µl RT reaction mixture (4 µl 5× First Strand Buffer (Invitrogen), 2 µl 100 mM DTT, 2 µl 10 mM dNTPs, 2 µl 50 mM MgCl$_2$, 1 µl RNAse Inhibitor (10 U/µl), 1 µl random primers (125 ng/µl, Invitrogen), 2 µl M-MLV reverse transcriptase (Invitrogen), water for the remaining volume). One µl of the RT product was then added to 24 µl of qPCR reaction and processed as described in Example 5 above, probing for human 18S ribosomal RNA cDNA. A negative control tube (without RT enzyme) was labeled as −RT. Results are shown in FIG. 12.

A separate fresh saliva sample was processed exactly as described above. The top aqueous phase was removed and 3 µl was directly added to 18 µl RT reaction mixture (described above). Two µl of the RT product was then added to 23 µl of qPCR reaction and processed as described in Example 5 above, probing for human 18S ribosomal RNA cDNA. A negative control tube (without reverse transcriptase enzyme) is labeled as −RT. Results are shown in FIG. 11. In both cases (FIGS. 12 and 13), the results show that human 18S ribosomal RNA could be detected in the aqueous phase of a lysed saliva sample treated with the detergent removal composition. As expected, the use of 3 µl in the RT reaction and 2 µl in the qPCR reaction (FIG. 13), instead of 1 µL and 1 µL, respectively (FIG. 12), produced more 18S ribosomal RNA cDNA in the RT reaction, as evidenced by the lower Ct value in the PCR reaction. The significant increase in RT product, and consequently qPCR product, with larger volumes of aqueous phase demonstrated the remarkable effectiveness of the detergent removal composition in the segregation of inhibitors to the lower organic phase. The −RT signal was due to the presence of human genomic DNA, which was not removed in these studies.

Blood

Human venous blood was collected in standard EDTA tubes. One volume of blood was mixed with 9 volumes of lysis buffer (4% SDS, 250 mM LiCl). Lysed blood was digested with PK at 60° C. for 15 mM; PK was then inactivated at 90° C. for 15 minutes. Removal of the SDS from a 100 µl aliquot of lysed blood was carried out by mixing 5 µl 2M ammonium chloride and 20 µl of a 1:0.8 (vol/vol) mixture of 1-pentanol and (poly)chlorotrifluoroethylene. The tube was vortexed vigorously for 2 minutes and centrifuged at 13,000 rpm for 2 minutes. The top (aqueous) phase was removed and an aliquot run in 1% agarose gel (FIG. 14). The nucleic acids were stained with SybrGold. Bands corresponding to human 18S and 28S ribosomal RNA can be seen. One µl of blood aqueous phase was added to 20 µl RT reaction mixture (4 µl 5× First Strand Buffer (Invitrogen), 2 µl 100 mM DTT, 2 µl 10 mM dNTPs, 2 µl 50 mM MgCl$_2$, 1 µl RNAse Inhibitor (10 U/µl), 1 µl random primers (125 ng/µl, Invitrogen), 1.5 µl M-MLV reverse transcriptase (Invitrogen), water for the remaining volume). One µl of RT product was then added to 24 µl of qPCR reaction and processed as described in Example 5 above. Negative control tube without reverse transcriptase enzyme is labeled as −RT. Results, shown in FIG. 15, clearly demonstrated that, once SDS, with potentially additional inhibitors bound to SDS, was removed by the detergent removal composition, human 18S ribosomal RNA could be detected by RT-PCR.

Example 8: Comparison of Alcohols

Several representative alcohols were investigated for their ability to perform in the detergent removal composition. Primary alcohols, secondary alcohols, cyclic alcohols, diols and both solid and liquid alcohols (at room temperature) were tested. Alcohols were tested either on a raw biological sample and/or in a "model system" whereby a simple water and SDS (4% wt/vol) mixture was used. In order to have effective phase separation the alcohol must be largely immiscible in water yet be soluble with the halocarbon. Results are summarized as follows:

| Alcohol | Halocarbon | Salt | Sample Type | Result |
|---|---|---|---|---|
| 1-propanol | BDCM | NH$_4$Cl | Model System | No phase separation |
| 1,2-propanediol | BDCM | NH$_4$Cl | Blood | No phase separation |
| 1-butanol | BDCM | NH$_4$Cl | Blood | Separation with clear aqueous phase; successful qPCR |

| Alcohol | Halocarbon | Salt | Sample Type | Result |
| --- | --- | --- | --- | --- |
| 3-methyl-1-butanol | BDCM | NH$_4$Cl | Blood | Separation with clear aqueous phase |
| 1-pentanol | BDCM | NH$_4$Cl | i) Model system; ii)Blood | i) Separation with clear aqueous phase ii) Separation with clear aqueous phase; successful qPCR |
| 4-methyl-2-pentanol | BDCM | NH$_4$Cl | Blood | Separation with clear aqueous phase |
| Cyclopentanol | BDCM | NH$_4$Cl | Blood | Separation with clear aqueous phase, successful qPCR |
| 1,2-hexanediol | BDCM | NH$_4$Cl | Blood | Separation with clear aqueous phase |
| 1-hexanol | BDCM | NH$_4$Cl | Blood | Separation with clear aqueous phase; successful qPCR |
| 1-heptanol | Poly(chlorotrifluoroethylene) | NH$_4$Cl | Blood | Separation with clear aqueous phase |
| 2-nonanol | BDCM | NH$_4$Cl | i) Model System ii) Blood | i) Separation with clear aqueous phase ii) Separation with clear aqueous phase; successful qPCR |
| 1-undecanol | BDCM | NH$_4$Cl | Blood | Separation achieved with increased salt concentration resulting in clear aqueous phase |
| 1-tetradecanol | BDCM | NH$_4$Cl | Blood | Separation achieved with increased salt concentration resulting in cloudy aqueous phase. This was considered an unsatisfactory result. |

As can be inferred from the observations obtained above, the water immiscible alcohol can be any alcohol with the structure of Formula I $$R^1\text{—OH} \qquad \qquad \text{I}$$

where $R^1$ is an optionally substituted, linear, branched or cyclic $C_4$-$C_{12}$ alkyl.

Example 9: Removal of Protein from an Aqueous Sample

Human venous blood was collected in a standard EDTA tube. One volume of blood was mixed thoroughly with 3 volumes of lysis buffer containing 4% SDS and 30 mM DTT. Detergent and protein removal was carried out as follows. NH$_4$Cl was added to a final concentration of 100 mM to 100 µl aliquots of the lysed blood sample. To each aliquot of lysed blood was added 20 µl of detergent removal composition containing varying amounts of 1-pentanol and BDCM (see details below). The tubes were vortexed vigorously for 2 minutes and centrifuged at 13,000 rpm for 2 minutes. The initial lysed blood samples (i.e., prior to detergent removal), as well as aqueous phases after detergent removal, were analysed by SDS-PAGE. The polyacrylamide gels were stained with Coomassie blue to reveal the protein bands. Results are shown in FIG. 16. Lane 1 contains the protein molecular weight marker. Lane 2 is empty. Lane 3 contains 0.5 µl of lysed blood sample prior to detergent removal. Lane 4 is empty. Lane 5 contains 1 µl of lysed blood sample prior to detergent removal. Lane 6 is empty. Lane 7 contains 7.5 µl of aqueous phase after treatment of lysed blood sample with BDCM only. Lane 8 is empty. Lane 9 contains 7.5 µl of aqueous phase after treatment of a lysed blood sample with a 3:7 (vol/vol) mix of 1-pentanol: BDCM. Lane 10 contains 7.5 µl of aqueous phase after treatment of a lysed blood sample with a 1:1 (vol/vol) mix of 1-pentanol: BDCM. Lane 11 contains 7.5 µl of aqueous phase after treatment of a lysed blood sample with a 7:3 (vol/vol) mix of 1-pentanol: BDCM. Lane 12 contains 7.5 µl of aqueous phase after treatment of lysed blood sample with 1-pentanol only.

The results show that very little or no protein was present in Lanes 9, 10 and 11 where the samples were treated with the detergent removal composition. This remarkably efficient extraction of proteins is very surprising. It shows that as little as $\frac{1}{5}^{th}$ volume of the detergent removal composition (i.e., 20 µl added to 100 µl of lysed blood sample) can very effectively remove the vast majority of protein from blood. The removal of the dark red color of hemoglobin that was observed (data not shown) is another indication of the unexpectedly powerful deproteinizing power of the detergent removal composition for samples containing SDS. The protein bands visible in lanes 3, 5, 7 and 12, where the detergent removal composition of the present application was not used (lanes 3 and 5) or some component was left out (lanes 7 and 12), indicates that all three components are essential for good results.

Example 10: Removal of Sarkosyl from a Biological Sample and Use of DNA in qPCR To demonstrate the effectiveness of the present method and composition for detergent removal in an aqueous composition containing a biological sample, a fresh human saliva sample was collected in a 15 ml conical tube. One milliliter of saliva was treated with an equal volume of lysis buffer containing 4% Sarkosyl and digested with Proteinase K ("PK") at 60° C. for 15 minutes. PK was inactivated by heating at 90° C. for 15 minutes and a 90 µl aliquot of the treated saliva in lysis buffer was mixed with 10.00 µl of a 2 M ammonium chloride solution.

Detergent removal was carried out by adding 20 µl of a 1:0.8 mixture of 1-pentanol and (poly)chlorotrifluoroethylene to 100 µl of the treated saliva sample. The tube was vortexed vigorously for 2 minutes and centrifuged at 13,000 rpm for 2 minutes. The top (aqueous) phase was removed and 4 µl was added to a human 18s-165 bp PCR reaction according to the method described in Example 5 above. Data for 4 µl of saliva-derived aqueous phase directly added to total of 25 µl of the qPCR reaction is shown in FIG. 17.

Example 11: Use of DNA in Biological Samples for the Construction of Library Preps Following Detergent Removal A key element of next-generation sequencing (NGS) is high-quality library preparation. The majority of high-throughput NGS library construction workflows depend upon a common series of steps, some of which are accomplished enzymatically—DNA fragmentation, end repair, A-tailing, adapter ligation, and PCR amplification. Input DNA quality is also an important determinant of library construction success. Enzymatic inhibitors, such as detergents, carried over during purification of biological samples can lead to reduced final yield, failure of the library prep, or low and uneven coverage when analyzed bioinformatically. Ideally, extraction protocols or systems should be optimized to purify inhibitor-free nucleic acids.

In this example, DNA was purified from biological samples by two different methods and the isolated DNA was used directly in the construction of library preps for NGS. The quality of the sequencing library preps was directly correlated to the effectiveness of inhibitor removal by the DNA purification methods tested. In one method, saliva was collected from 2 donors into an equal volume of Oragene® (DNA Genotek, Ottawa, Canada), a DNA extraction and purification reagent that contains detergent and other sequencing inhibitors, followed by the addition of prepIT·L2P (DNA Genotek), a reagent and method designed to remove inhibitors of downstream analysis, and finally followed by ethanol precipitation to recover purified DNA. In the second method, aliquots of the same saliva collected into Oragene were simply mixed with the composition of the present invention. Specifically, 100 μl of saliva/Oragene was mixed with 10 μl 2M $NH_4Cl$ and 20 μl of pentanol:Halocarbon Oil 6.3 (1:0.8 (v/v)) and allowed to settle for 20 minutes. The resulting supernatant, containing nucleic acids, was transferred to a clean tube ready for library prep construction (Illumina's Nextera® XT DNA Library Preparation Guide).

Sequencing libraries were prepared from Oragene/saliva samples treated with the present composition ("STAT") and from purified DNA extracted using Oragene/prepIT·L2P. Prepared libraries were analyzed on an Agilent 2100 Bioanalyzer using the Agilent High Sensitivity DNA Kit. Bioanalyzer gel images (FIG. 18a-b) and traces (FIG. 19 a-d) show that libraries prepared from saliva samples in which the detergent and other inhibitors have been removed using STAT have the same mean fragment size and fragment length distribution, and a similar concentration as the libraries prepared from purified DNA. Hence, the supernatant of STAT-treated biological samples can be used directly in the construction of library preparations for NGS, saving considerable time and expense.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments in which an exclusive property or privilege is claimed are defined as follows:

1. A method of removing a detergent from an aqueous solution comprising said detergent, said method comprising the step of mixing the aqueous solution with:
    a. a salt;
    b. a water immiscible alcohol of Formula I $R^1$—OH          (Formula I)

where $R^1$ is an optionally substituted, linear, branched or cyclic $C_4$-$C_{12}$ alkyl; and
    c. a water immiscible halocarbon, wherein said halocarbon is miscible with said alcohol of Formula I,
    to form a two-phase mixture comprising an aqueous phase and a non-aqueous phase, wherein more than 99% wt/vol of the detergent is in the non-aqueous phase; and
        wherein the halocarbon is present at a concentration sufficient to increase the density of the non-aqueous phase to greater than the density of the aqueous phase,
        wherein the concentration of halocarbon in the alcohol is up to 80% (v/v),
        wherein the ratio of the total volume of the salt plus the alcohol plus the halocarbon to the volume of the aqueous solution comprising the detergent is from 1:9 to 2:1.

2. The method of claim 1, wherein the detergent is an anionic detergent.

3. The method of claim 1, wherein the method further removes a detergent-associated and/or detergent-bound molecule from the aqueous solution; optionally, wherein the detergent-associated and/or detergent-bound molecule is a protein.

4. The method of claim 1, wherein the alcohol and the halocarbon are combined prior to mixing with the aqueous solution;
    optionally, wherein the method additionally comprises the step of separating the aqueous phase from the two-phase mixture;
    optionally, wherein the method additionally comprises the step of centrifuging the mixture to facilitate separation of the two phases.

5. The method of claim 1, wherein the method comprises one or more of the following characteristics:
    the concentration of the salt in the aqueous phase of said two-phase mixture is from 30 mM to 0.5 M; and
    the concentration of halocarbon in the alcohol is up to 50% (v/v).

6. The method of claim 1, wherein the ratio of the total volume of the salt plus the alcohol plus the halocarbon to the volume of the aqueous solution comprising the detergent is 1:5.

7. The method of claim 1, further comprising the step of directly using a portion of the aqueous phase from the two-phase mixture for a downstream application selected from a polymerase chain reaction (PCR), library preparation, or nucleotide sequencing; wherein the PCR is optionally RT-PCR.

8. The method of claim 1, wherein the aqueous phase of the two-phase mixture comprises <0.01% wt/vol of the detergent.

9. The method of claim 1, wherein the method comprises one or more of the following characteristics:
    (a) the salt is a quaternary ammonium salt or an alkali metal salt; optionally, wherein the salt is ammonium acetate, ammonium chloride, ammonium sulfate, a betaine salt, choline chloride, diethylamine hydrochloride, dimethylethanolamine, ethanolamine, ethylammonium chloride, methylammonium chloride, tetra-n-butylammonium acetate, tetraethylammonium chloride monohydrate, tetramethylammonium chloride, tetra-n-propylammonium chloride, methyltri-n-butylammonium chloride, triethylamine hydrochloride, triethylmethylammonium chloride, trimethylamine hydrochloride, an acid salt of 1-butylamine, an acid salt of 1-pentylamine, an acid salt of 1-hexylamine, an acid salt of 1-dodecylamine, lithium chloride; sodium chloride, potassium chloride, or a combination thereof;
(b) the water immiscible alcohol is 1-butanol, 3-methyl-1-butanol, 2-butanol, 1-heptanol, 1,2-hexanediol, 1-hexanol, 2-nonanol, 1-pentanol, 4-methyl-2-pentanol, cyclopentanol, 1-undecanol or a combination thereof;
(c) the halocarbon is 1-bromo-3-chloropropane, 1-bromo-6-chlorohexane, bromodichloromethane (BDCM), chlorodibromomethane, chloroform, 2-iodopropane, poly(chlorotrifluoroethylene), or a combination thereof; and
(d) the detergent is sodium dodecyl sulfate (SDS).

10. The method of claim 1, wherein the method comprises one or more of the following characteristics:
(a) the salt is ammonium chloride;
(b) the water immiscible alcohol is 1-butanol, 1-pentanol, cyclopentanol, 1-hexanol, 1-heptanol, 2-nonanol or 1-undecanol; and
(c) the halocarbon is BDCM or polychlorotrifluoroethylene.

11. The method of claim 1, wherein the aqueous solution is a biological sample; optionally, wherein the biological sample is a modified biological sample comprising a sample storage, lysis or extraction composition.

12. The method of claim 1, wherein the salt is ammonium chloride, the alcohol is 1-pentanol, and the halocarbon is bromodichloromethane or polychlorotrifluoroethylene.

13. The method of claim 1, wherein the method comprises one or more of the following characteristics:
(a) a reducing agent; optionally, wherein the reducing agent is dithiothreitol (DTT), mercaptohexanol, mercaptoundecanol, dimercaptopropanol or mercaptobutanol;
(b) a chelator and/or a buffer; optionally, wherein the chelator is ethylene glycol tetraacetic acid (EGTA), (2-Hydroxyethyl)ethylenediaminetriacetic acid (HEDTA), diethylene triamine pentaacetic acid (DTPA), NitriloTriAcetic Acid (NTA), ethylenediaminetriacetic acid (EDTA), cyclohexanediaminetetraacetic acid (CDTA), citrate anhydrous, sodium citrate, calcium citrate, ammonium citrate, ammonium bicitrate, citric acid, diammonium citrate, ferric ammonium citrate, lithium citrate, or any combination thereof; and
(c) a lipophilic stain; optionally, wherein the lipophilic stain is Nile Red, 9-Anthryldiazomethane, Fluorol Yellow 088, N,N,N-Trimethyl-4-(6-phenyl-1,3,5-hexatrien-1-yl) phenylammonium p-toluenesulfonate (TMA-DPH), 3,3'-Dioctadecyloxacarbocyanine percholorate, 1,6-Diphenyl-1,3,5-hexatriene, Sudan III, Sudan Orange G, Nile Blue chloride or Solvent Blue 37.

14. The method of claim 1, wherein the aqueous solution comprising said detergent has a concentration of detergent up to 10% (w/v),
wherein, following the step of mixing the aqueous solution with the salt, the water immiscible alcohol of Formula I, and the water immiscible halocarbon to form the two-phase mixture:
the concentration of the salt in the aqueous phase of said two-phase mixture is from 30 mM to 0.5 M, and
the aqueous phase of the two-phase mixture comprises <0.01% wt/vol of the detergent.

* * * * *